(12) United States Patent
Wu et al.

(10) Patent No.: US 12,129,296 B2
(45) Date of Patent: Oct. 29, 2024

(54) ANTI-HUMAN CLAUDIN 18.2 MONOCLONAL ANTIBODY AND APPLICATION THEREOF

(71) Applicant: REYOUNG (SUZHOU) BIOLOGY SCIENCE & TECHNOLOGY CO., LTD, Jiangsu (CN)

(72) Inventors: Yanyan Wu, Jiangsu (CN); Wenjun Cui, Jiangsu (CN); Chenfei Hu, Jiangsu (CN)

(73) Assignee: REYOUNG (SUZHOU) BIOLOGY SCIENCE & TECHNOLOGY CO., LTD, Jiangsu (CN)

( * ) Notice: Subject to any disclaimer, the term of this patent is extended or adjusted under 35 U.S.C. 154(b) by 900 days.

(21) Appl. No.: 17/267,637

(22) PCT Filed: Aug. 21, 2019

(86) PCT No.: PCT/CN2019/101785
§ 371 (c)(1),
(2) Date: Feb. 10, 2021

(87) PCT Pub. No.: WO2020/038404
PCT Pub. Date: Feb. 27, 2020

(65) Prior Publication Data
US 2021/0261658 A1    Aug. 26, 2021

(30) Foreign Application Priority Data

Aug. 22, 2018    (CN) .......................... 201810958670.2
Aug. 20, 2019    (CN) .......................... 201910767966.0

(51) Int. Cl.
C07K 16/28    (2006.01)
A61P 35/00    (2006.01)
A61K 39/00    (2006.01)

(52) U.S. Cl.
CPC .............. *C07K 16/28* (2013.01); *A61P 35/00* (2018.01); *A61K 2039/505* (2013.01); *C07K 2317/24* (2013.01); *C07K 2317/732* (2013.01); *C07K 2317/734* (2013.01)

(58) Field of Classification Search
CPC ................ C07K 16/28; C07K 2317/24; C07K 2317/732; C07K 2317/734; A61P 35/00; A61K 2039/505
See application file for complete search history.

(56) References Cited

U.S. PATENT DOCUMENTS

2013/0236467 A1 *    9/2013    Griggs ................. C07K 16/247
                                                                435/254.2

FOREIGN PATENT DOCUMENTS

| CA | 3030257 A1 * | 1/2018 | ........... A61K 31/282 |
|---|---|---|---|
| CN | 104321345 A | 1/2015 | |
| CN | 105073776 A | 11/2015 | |
| CN | 107667118 A | 2/2018 | |
| CN | 107960056 A | 4/2018 | |
| WO | 2013167259 A1 | 11/2013 | |
| WO | 2013174510 A1 | 11/2013 | |

OTHER PUBLICATIONS

Yin, H et. al. "Non-viral vectors for gene-based therapy", 2014, Nature Reviews, 15, 541-555. (Year: 2014).*
International Search Report dated Nov. 20, 2019 from PCT Application No. PCT/CN1029/101785.
Klamp, T. et al. "Highly Specific Auto-Antibodies against Claudin-18 Isoform 2 Induced by a Chimeric HBcAg Virus-Like Particle Vaccine Kill Tumor Cells and Inhibit the Growth of Lung Metastases." Cancer Research, vol. 71, No. (2), Jan. 11, 2011 (Jan. 11, 2011), pp. 516-527.
Sahin, U. et al. "Claudin-18 Splice Variant 2 is a Pan-Cancer Target Suitable for Therapeutic Antibody Development." Human Cancer Biology., vol. 14, No. (23), Dec. 1, 2008 (Dec. 1, 2008), pp. 7624-7634.
Woll. S. et al. "Claudin 18.2 is a Target for IMAB362 Antibody in Pancreatic Neoplasms." International Journal of Cancer, vol. vol. 134, Jul. 30, 2013 (Jul. 30, 2013), pp. 731-739.
Y Sanada N Oue Y Mitani K Yoshida H Nakayama W Yasui. "Down-regulation of the claudin-18 gene, identified through serial analysis of gene expression data analysis, in gastric cancer with an intestinal phenotype". The Journal of Pathology, 2006, 208(5): 633-642. Published in USA.

* cited by examiner

*Primary Examiner* — Nelson B Moseley, II
*Assistant Examiner* — Alyssa Rae Stonebraker
(74) *Attorney, Agent, or Firm* — INNOVATION CAPITAL LAW GROUP, LLP; Vic Lin

(57) ABSTRACT

Provided are an anti-human claudin 18.2 monoclonal antibody and application thereof. The antibody has three heavy chain CDRs and three light chain CDRs, one of the three heavy chain CDRs and three light chain CDRs is as follows: a heavy chain CDR1 is SEQ ID NO: 1, a heavy chain CDR2 is SEQ ID NO: 2, a heavy chain CDR3 is SEQ ID NO: 3, a light chain CDR1 is SEQ ID NO: 4, a light chain CDR2 is SEQ ID NO: 5, and a light chain CDR3 is SEQ ID NO: 6.

12 Claims, 3 Drawing Sheets
Specification includes a Sequence Listing.

ANTI-HUMAN CLAUDIN 18.2 MONOCLONAL ANTIBODY AND APPLICATION THEREOF

REFERENCE TO SEQUENCE LISTING SUBMITTED ELECTRONICALLY

The official copy of the sequence listing is submitted electronically via EFS-Web as an ASCII formatted sequence listing with a file named "NIN1-PAU16NS-Sequence-Listing.txt", created on 2021 Feb. 8, and having a size of 46 kilobytes and is filed concurrently with the specification. The sequence listing contained in this ASCII formatted document is part of the specification and is herein incorporated by reference in its entirety.

BACKGROUND OF THE INVENTION

1. Technical Field

The present invention relates to the field of biomedicine, in particular to an anti-human claudin 18.2 monoclonal antibody and an application thereof.

2. Description of Related Art

The claudin family is the skeleton protein for tight junctions between epithelial cells and participates in the formation of tight junctions. The tight junctions maintain the polar arrangement and barrier function of cells. Their abnormal expression leads to the destruction of tight junction structures and functions, which is the basis of many diseases. Studies have shown that the claudin family is abnormally expressed in a variety of tumors of epithelial origin and closely related to the occurrence and development of these tumors, thus having broad application prospects in diagnosis, treatment, and prognostic judgment. Therefore, the claudin family has become a new hot spot in tumor research.

The human-derived claudin 18 gene has two different first exons, so two subtypes Claudin 18.1 and Claudin 18.2 can be produced. These two molecules are different in the structure of the N-terminal 69 amino acids, located in the ring structure of the first extracellular region. The two subtypes of claudin 18 are transcriptionally amplified in different tissues. Claudin 18.1 is mainly expressed in lung tissue and Claudin 18.2 is specifically expressed in stomach tissue.

In 2006, Sanada et al., found that the expression of claudin-18 gene was down-regulated in 57% of gastric cancers. Through immunohistochemical analysis, claudin-18 was expressed on normal gastric mucosa and the cell membrane of duodenal Paneth cells; however, in some intestinal metaplasia and 90% of gastric adenomas, the claudin-18 expression was reduced; moreover, the expression reduction was more common in intestinal gastric cancer than in other types of gastric cancer, and it was speculated that it may be involved in the occurrence of early gastric cancer. Survival analysis showed that the reduction of claudin-18 expression in gastric cancer was related to the poor prognosis of advanced patients, and it was believed that the reduction of claudin-18 expression was a factor for the poor prognosis of patients with a gastric cancer.

In 2008, a study by Sahin et al., confirmed that Claudin 18.2 was expressed in 77% of primary gastric adenocarcinoma tissues. It is extremely important that 56% of the tissues have an expression level of 60% or above. Consistent with the above research results, the expression of Claudin 18.2 protein in intestinal gastric cancer was down-regulated; however, the expression of Claudin 18.2 protein in diffuse gastric cancer was higher. However, no claudin 18.2 protein expression is in the pancreas, esophagus, ovary and other tissues under normal conditions, and the corresponding tumor tissues can express claudin 18.2 protein in a large quantity. Therefore, claudin 18.2 protein can be used as a target site for clinical tumor diagnosis and treatment. However, there is no antibody developed with this protein as a target site.

BRIEF SUMMARY OF THE INVENTION

The invention provides an anti-human claudin 18.2 monoclonal antibody with good specificity, high affinity and stability.

A first objective of the present invention is to provide an amino acid sequence of an anti-human claudin18.2 monoclonal antibody, specifically as follows:

An anti-human claudin18.2 monoclonal antibody, having three heavy chain complementarity-determining regions (heavy chain CDR1, heavy chain CDR2, and heavy chain CDR3) and three light chain complementarity-determining regions (light chain CDR1, light chain CDR2, and light chain CDR3), the heavy chain CDR1 is one of: SEQ ID NO: 1, SEQ ID NO: 7, SEQ ID NO: 13, SEQ ID NO: 19, SEQ ID NO:25; SEQ ID NO: 31, SEQ ID NO: 37, SEQ ID NO: 43, SEQ ID NO:49, SEQ ID NO:55, SEQ ID NO:61, SEQ ID NO:67, and SEQ ID NO:73, or a similar sequence having a homology of more than 50% with one of the above sequences;

the heavy chain CDR2 is one of: SEQ ID NO: 2, SEQ ID NO: 8, SEQ ID NO: 14, SEQ ID NO:20, SEQ ID NO:26, SEQ ID NO: 32, SEQ ID NO: 38, SEQ ID NO: 44, SEQ ID NO:50, SEQ ID NO:56, SEQ ID NO:62, SEQ ID NO:68, and SEQ ID NO:74, or a similar sequence having a homology of more than 50% with one of the above sequences;

the heavy chain CDR3 is one of: SEQ ID NO: 3, SEQ ID NO: 9, SEQ ID NO: 15, SEQ ID NO: 21, SEQ ID NO:27; SEQ ID NO: 33, SEQ ID NO: 39, SEQ ID NO: 45, SEQ ID NO:51, SEQ ID NO:57, SEQ ID NO:63, SEQ ID NO:69, and SEQ ID NO:75, or a similar sequence having a homology of more than 50% with one of the above sequences;

the light chain CDR1 is one of: SEQ ID NO: 4, SEQ ID NO: 10, SEQ ID NO: 16, SEQ ID NO:22, SEQ ID NO:28, SEQ ID NO: 34, SEQ ID NO: 40, SEQ ID NO: 46, SEQ ID NO:52, SEQ ID NO:58, SEQ ID NO:64, SEQ ID NO:70, and SEQ ID NO:76, or a similar sequence having a homology of more than 50% with one of the above sequences;

the light chain CDR2 is one of: SEQ ID NO: 5, SEQ ID NO: 11, SEQ ID NO: 17, SEQ ID NO:23, SEQ ID NO:29, SEQ ID NO:35, SEQ ID NO: 41, SEQ ID NO: 47, SEQ ID NO:53, SEQ ID NO:59, SEQ ID NO:65, SEQ ID NO:71, and SEQ ID NO:77, or a similar sequence having a homology of more than 50% with one of the above sequences;

the light chain CDR3 is one of: SEQ ID NO: 6, SEQ ID NO: 12, SEQ ID NO: 18, SEQ ID NO:24, SEQ ID NO:30, SEQ ID NO: 36, SEQ ID NO: 42, SEQ ID NO: 48, SEQ ID NO:54, SEQ ID NO:60, SEQ ID NO:66, SEQ ID NO:72, and SEQ ID NO:78, or a similar sequence having a homology of more than 50% with one of the above sequences.

Preferably, the heavy chain CDR1 is SEQ ID NO: 1, the heavy chain CDR2 is SEQ ID NO: 2, the heavy chain CDR3 is SEQ ID NO: 3, the light chain CDR1 is SEQ ID NO: 4, the light chain CDR2 is SEQ ID NO: 5, and the light chain CDR3 is SEQ ID NO: 6; or the heavy chain CDR1 is SEQ ID NO: 7, the heavy chain CDR2 is SEQ ID NO: 8, the heavy chain CDR3 is SEQ ID NO: 9, the light chain CDR1 is SEQ ID NO: 10, the light chain CDR2 is SEQ ID NO: 11, and the light chain CDR3 is SEQ ID NO: 12; or the heavy chain CDR1 is SEQ ID NO: 13, the heavy chain CDR2 is SEQ ID NO: 14, the heavy chain CDR3 is SEQ ID NO: 15, the light chain CDR1 is SEQ ID NO: 16, the light chain CDR2 is SEQ ID NO: 17, and the light chain CDR3 is SEQ ID NO: 18; or the heavy chain CDR1 is SEQ ID NO: 19, the heavy chain CDR2 is SEQ ID NO: 20, the heavy chain CDR3 is SEQ ID NO: 21, the light chain CDR1 is SEQ ID NO: 22, the light chain CDR2 is SEQ ID NO: 23, and the light chain CDR3 is SEQ ID NO: 24; or the heavy chain CDR1 is SEQ ID NO: 25, the heavy chain CDR2 is SEQ ID NO: 26, the heavy chain CDR3 is SEQ ID NO: 27, the light chain CDR1 is SEQ ID NO: 28, the light chain CDR2 is SEQ ID NO: 29, and the light chain CDR3 is SEQ ID NO: 30; or the heavy chain CDR1 is SEQ ID NO: 31, the heavy chain CDR2 is SEQ ID NO: 32, the heavy chain CDR3 is SEQ ID NO: 33, the light chain CDR1 is SEQ ID NO: 34, the light chain CDR2 is SEQ ID NO:35, and the light chain CDR3 is SEQ ID NO: 36; or the heavy chain CDR1 is SEQ ID NO: 37, the heavy chain CDR2 is SEQ ID NO: 38, the heavy chain CDR3 is SEQ ID NO: 39, the light chain CDR1 is SEQ ID NO: 40, the light chain CDR2 is SEQ ID NO: 41, and the light chain CDR3 is SEQ ID NO: 42; or the heavy chain CDR1 is SEQ ID NO: 43, the heavy chain CDR2 is SEQ ID NO: 44, the heavy chain CDR3 is SEQ ID NO: 45, the light chain CDR1 is SEQ ID NO: 46, the light chain CDR2 is SEQ ID NO: 47, and the light chain CDR3 is SEQ ID NO: 48; or the heavy chain CDR1 is SEQ ID NO: 49, the heavy chain CDR2 is SEQ ID NO: 50, the heavy chain CDR3 is SEQ ID NO: 51, the light chain CDR1 is SEQ ID NO: 52, the light chain CDR2 is SEQ ID NO: 53, and the light chain CDR3 is SEQ ID NO: 54; or the heavy chain CDR1 is SEQ ID NO: 55, the heavy chain CDR2 is SEQ ID NO: 56, the heavy chain CDR3 is SEQ ID NO: 57, the light chain CDR1 is SEQ ID NO: 58, the light chain CDR2 is SEQ ID NO: 59, and the light chain CDR3 is SEQ ID NO: 60; or the heavy chain CDR1 is SEQ ID NO: 61, the heavy chain CDR2 is SEQ ID NO: 62, the heavy chain CDR3 is SEQ ID NO: 63, the light chain CDR1 is SEQ ID NO: 64, the light chain CDR2 is SEQ ID NO: 65, and the light chain CDR3 is SEQ ID NO: 66; or the heavy chain CDR1 is SEQ ID NO: 67, the heavy chain CDR2 is SEQ ID NO: 68, the heavy chain CDR3 is SEQ ID NO: 69, the light chain CDR1 is SEQ ID NO: 70, the light chain CDR2 is SEQ ID NO:71, and the light chain CDR3 is SEQ ID NO: 72; or the heavy chain CDR1 is SEQ ID NO: 73, the heavy chain CDR2 is SEQ ID NO: 74, the heavy chain CDR3 is SEQ ID NO: 75, the light chain CDR1 is SEQ ID NO: 76, and the light chain CDR2 is SEQ ID NO: 77, and the light chain CDR3 is SEQ ID NO:78. Preferably, the heavy chain variable region comprises the above-mentioned heavy chain CDR1, CDR2 and CDR3; the light chain variable region comprises the above-mentioned light chain CDR1, CDR2 and CDR3.

Preferably, the amino acid sequence of the light chain variable region is one of SEQ ID NO: 79, SEQ ID NO: 81, SEQ ID NO:83; SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, and SEQ ID NO: 103;

preferably, the amino acid sequence of the light chain variable region is one of: SEQ ID NO: 80, SEQ ID NO: 82, SEQ ID NO:84; SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, and SEQ ID NO: 104.

Preferably,
the amino acid sequence of the heavy chain variable region is SEQ ID NO: 79, and the amino acid sequence of the light chain variable region is SEQ ID NO: 80; or
the amino acid sequence of the heavy chain variable region is SEQ ID NO: 81, and the amino acid sequence of the light chain variable region is SEQ ID NO: 82; or
the amino acid sequence of the heavy chain variable region is SEQ ID NO: 83, and the amino acid sequence of the light chain variable region is SEQ ID NO: 84; or
the amino acid sequence of the heavy chain variable region is SEQ ID NO: 85, and the amino acid sequence of the light chain variable region is SEQ ID NO: 86; or
the amino acid sequence of the heavy chain variable region is SEQ ID NO: 87, and the amino acid sequence of the light chain variable region is SEQ ID NO: 88; or
the amino acid sequence of the heavy chain variable region is SEQ ID NO: 89, and the amino acid sequence of the light chain variable region is SEQ ID NO: 90; or
the amino acid sequence of the heavy chain variable region is SEQ ID NO: 91, and the amino acid sequence of the light chain variable region is SEQ ID NO: 92; or
the amino acid sequence of the heavy chain variable region is SEQ ID NO: 93, and the amino acid sequence of the light chain variable region is SEQ ID NO: 94; or
the amino acid sequence of the heavy chain variable region is SEQ ID NO: 95, and the amino acid sequence of the light chain variable region is SEQ ID NO: 96; or
the amino acid sequence of the heavy chain variable region is SEQ ID NO: 97, and the amino acid sequence of the light chain variable region is SEQ ID NO: 98; or
the amino acid sequence of the heavy chain variable region is SEQ ID NO: 99, and the amino acid sequence of the light chain variable region is SEQ ID NO: 100; or
the amino acid sequence of the heavy chain variable region is SEQ ID NO: 101, and the amino acid sequence of the light chain variable region is SEQ ID NO: 102; or
the amino acid sequence of the heavy chain variable region is SEQ ID NO: 103, and the amino acid sequence of the light chain variable region is SEQ ID NO: 104.

Preferably, the amino acid sequence of the heavy chain variable region is a similar sequence having a homology of at least 50% with sequence a, and the sequence a is one of: SEQ ID NO: 79, SEQ ID NO: 81, SEQ ID NO: 83, SEQ ID NO: 85; SEQ ID NO:87, SEQ ID NO: 89, SEQ ID NO: 91, SEQ ID NO: 93, SEQ ID NO: 95, SEQ ID NO: 97, SEQ ID NO: 99, SEQ ID NO: 101, and SEQ ID NO: 103.

Preferably, the amino acid sequence of the light chain variable region is a similar sequence having a homology of at least 50% with sequence b, and the sequence b is one of: SEQ ID NO: 80, SEQ ID NO: 82, SEQ ID NO: 84, SEQ ID NO: 86; SEQ ID NO:88, SEQ ID NO: 90, SEQ ID NO: 92, SEQ ID NO: 94, SEQ ID NO: 96, SEQ ID NO: 98, SEQ ID NO: 100, SEQ ID NO: 102, and SEQ ID NO: 104.

The amino acid sequence of the heavy chain includes heavy chain CDR1, heavy chain CDR2, heavy chain CDR3, light chain CDR1, light chain CDR2, and light chain CDR3; the heavy chain CDR1 is SEQ ID NO: 1, the heavy chain CDR2 is SEQ ID NO: 2, the heavy chain CDR3 is SEQ ID NO: 3, the light chain CDR1 is SEQ ID NO: 4, the light chain CDR2 is SEQ ID NO: 5, and the light chain CDR3 is SEQ ID NO: 6; or the heavy chain CDR1 is SEQ ID NO: 7, the heavy chain CDR2 is SEQ ID NO: 8, the heavy chain CDR3 is SEQ ID NO: 9, the light chain CDR1 is SEQ ID NO: 10, the light chain CDR2 is SEQ ID NO: 11, and the light chain CDR3 is SEQ ID NO: 12; or the heavy chain CDR1 is SEQ ID NO: 13, the heavy chain CDR2 is SEQ ID NO: 14, the heavy chain CDR3 is SEQ ID NO: 15, the light chain CDR1 is SEQ ID NO: 16, the light chain CDR2 is SEQ ID NO: 17, and the light chain CDR3 is SEQ ID NO: 18; or the heavy chain CDR1 is SEQ ID NO: 19, the heavy chain CDR2 is SEQ ID NO: 20, the heavy chain CDR3 is SEQ ID NO: 21, the light chain CDR1 is SEQ ID NO: 22, the light chain CDR2 is SEQ ID NO: 23, and the light chain CDR3 is SEQ ID NO: 24; or the heavy chain CDR1 is SEQ ID NO: 25, the heavy chain CDR2 is SEQ ID NO: 26, the heavy chain CDR3 is SEQ ID NO: 27, the light chain CDR1 is SEQ ID NO: 28, the light chain CDR2 is SEQ ID NO:29, and the light chain CDR3 is SEQ ID NO: 30; or the heavy chain CDR1 is SEQ ID NO: 31, the heavy chain CDR2 is SEQ ID NO: 32, the heavy chain CDR3 is SEQ ID NO: 33, the light chain CDR1 is SEQ ID NO: 34, the light chain CDR2 is SEQ ID NO: 35, and the light chain CDR3 is SEQ ID NO: 36; or the heavy chain CDR1 is SEQ ID NO: 37, the heavy chain CDR2 is SEQ ID NO: 38, the heavy chain CDR3 is SEQ ID NO: 39, the light chain CDR1 is SEQ ID NO: 40, the light chain CDR2 is SEQ ID NO: 41, and the light chain CDR3 is SEQ ID NO: 42; or the heavy chain CDR1 is SEQ ID NO: 43, the heavy chain CDR2 is SEQ ID NO: 44, the heavy chain CDR3 is SEQ ID NO: 45, the light chain CDR1 is SEQ ID NO: 46, the light chain CDR2 is SEQ ID NO: 47, and the light chain CDR3 is SEQ ID NO: 48; or the heavy chain CDR1 is SEQ ID NO: 49, the heavy chain CDR2 is SEQ ID NO: 50, the heavy chain CDR3 is SEQ ID NO: 51, the light chain CDR1 is SEQ ID NO: 52, the light chain CDR2 is SEQ ID NO: 53, and the light chain CDR3 is SEQ ID NO: 54; or the heavy chain CDR1 is SEQ ID NO: 55, the heavy chain CDR2 is SEQ ID NO: 56, the heavy chain CDR3 is SEQ ID NO: 57, the light chain CDR1 is SEQ ID NO: 58, the light chain CDR2 is SEQ ID NO: 59, and the light chain CDR3 is SEQ ID NO: 60; or the heavy chain CDR1 is SEQ ID NO: 61, the heavy chain CDR2 is SEQ ID NO: 62, the heavy chain CDR3 is SEQ ID NO: 63, the light chain CDR1 is SEQ ID NO: 64, the light chain CDR2 is SEQ ID NO:65, and the light chain CDR3 is SEQ ID NO: 66; or the heavy chain CDR1 is SEQ ID NO: 67, the heavy chain CDR2 is SEQ ID NO: 68, the heavy chain CDR3 is SEQ ID NO: 69, the light chain CDR1 is SEQ ID NO: 70, the light chain CDR2 is SEQ ID NO: 71, and the light chain CDR3 is SEQ ID NO: 72; or the heavy chain CDR1 is SEQ ID NO: 73, the heavy chain CDR2 is SEQ ID NO: 74, the heavy chain CDR3 is SEQ ID NO: 75, the light chain CDR1 is SEQ ID NO: 76, the light chain CDR2 is SEQ ID NO:77, and the light chain CDR3 is SEQ ID NO: 78.

Preferably, the amino acid sequence of the antibody includes the above-mentioned heavy chain variable region and light chain variable region.

A second objective of the present invention is to provide a nucleic acid sequence of the anti-human claudin 18.2 monoclonal antibody, specifically as follows:

A nucleic acid molecule, comprising a nucleic acid sequence capable of encoding a heavy chain CDR and/or a light chain CDR, wherein the heavy chain CDR1 is one of: SEQ ID NO: 1, SEQ ID NO: 7, SEQ ID NO: 13, SEQ ID NO: 19, SEQ ID NO:25; SEQ ID NO: 31, SEQ ID NO: 37, SEQ ID NO: 43, SEQ ID NO:49, SEQ ID NO:55, SEQ ID NO:61, SEQ ID NO:67, and SEQ ID NO:73, or a similar sequence having a homology of more than 50% with one of the above sequences;

the heavy chain CDR2 is one of: SEQ ID NO: 2, SEQ ID NO: 8, SEQ ID NO: 14, SEQ ID NO:20, SEQ ID NO:26, SEQ ID NO: 32, SEQ ID NO: 38, SEQ ID NO: 44, SEQ ID NO:50, SEQ ID NO:56, SEQ ID NO:62, SEQ ID NO:68, and SEQ ID NO:74, or a similar sequence having a homology of more than 50% with one of the above sequences;

the heavy chain CDR3 is one of: SEQ ID NO: 3, SEQ ID NO: 9, SEQ ID NO: 15, SEQ ID NO: 21, SEQ ID NO:27; SEQ ID NO: 33, SEQ ID NO: 39, SEQ ID NO: 45, SEQ ID NO:51, SEQ ID NO:57, SEQ ID NO:63, SEQ ID NO:69, and SEQ ID NO:75, or a similar sequence having a homology of more than 50% with one of the above sequences;

the light chain CDR1 is one of: SEQ ID NO: 4, SEQ ID NO: 10, SEQ ID NO: 16, SEQ ID NO:22, SEQ ID NO:28, SEQ ID NO: 34, SEQ ID NO: 40, SEQ ID NO: 46, SEQ ID NO:52, SEQ ID NO:58, SEQ ID NO:64, SEQ ID NO:70, and SEQ ID NO:76, or a similar sequence having a homology of more than 50% with one of the above sequences;

the light chain CDR2 is one of: SEQ ID NO: 5, SEQ ID NO: 11, SEQ ID NO: 17, SEQ ID NO:23, SEQ ID NO:29, SEQ ID NO:35, SEQ ID NO: 41, SEQ ID NO: 47, SEQ ID NO:53, SEQ ID NO:59, SEQ ID NO:65, SEQ ID NO:71, and SEQ ID NO:77, or a similar sequence having a homology of more than 50% with one of the above sequences;

the light chain CDR3 is one of: SEQ ID NO: 6, SEQ ID NO: 12, SEQ ID NO: 18, SEQ ID NO:24, SEQ ID NO:30, SEQ ID NO: 36, SEQ ID NO: 42, SEQ ID NO: 48, SEQ ID NO:54, SEQ ID NO:60, SEQ ID NO:66, SEQ ID NO:72, and SEQ ID NO:78, or a similar sequence having a homology of more than 50% with one of the above sequences.

A nucleic acid molecule, comprising a nucleic acid sequence capable of encoding a heavy chain variable region and/or a light chain variable region, wherein the amino acid sequence of the heavy chain variable region is one of: SEQ ID NO: 79, SEQ ID NO: 81, SEQ ID NO: 83, SEQ ID NO:85; SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, and SEQ ID NO: 103;

the amino acid sequence of the light chain variable region is one of: SEQ ID NO: 80, SEQ ID NO: 82, SEQ ID NO: 84, SEQ ID NO:86; SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, and SEQ ID NO: 104.

The present invention also provides a vector, comprising any one of the aforementioned nucleic acid molecules.

The present invention also provides a host cell, comprising the amino acid sequence according to any of the above or the nucleic acid molecule according to any of the above or comprising the above-mentioned vector.

The present invention further provides a conjugate comprising the antibody according to any of the above.

The present invention further provides a composition, comprising a main component and an auxiliary component, wherein the main component comprises one or more of the antibody according to any of the above, the nucleic acid molecule according to any of the above, the above-mentioned vector, the above-mentioned host cell, and the above-mentioned conjugate; the auxiliary component is selected from pharmaceutically acceptable carriers or excipients, and optionally other biologically active substances.

The other biologically active substances include, but are not limited to, other antibodies, fusion proteins or drugs (for example, anti-tumor drugs, such as radiotherapy and chemotherapy drugs).

The present invention further provides applications of the aforementioned antibody, nucleic acid molecule, vector, host cell, conjugate, and composition in the preparation of drugs or detection reagents for treating diseases.

The diseases refer to malignant tumors, cardiovascular disease or inflammatory diseases. The present invention further provides a diagnostic reagent or kit, comprising the antibody according to any of the above. The diagnostic reagent or kit is used for diagnosing diseases related to claudin 18.2 in vitro (for example, cells or tissues) or in vivo (for example, human or animal models).

The present invention is further described as follows: In the present invention, unless otherwise specified, the scientific and technical terms used herein have the meanings commonly understood by those skilled in the art. In addition, protein, terms related to nucleic acid chemistry, molecular biology, cell and tissue culture, microbiology, and immunology, and laboratory procedures used herein are all terms and routine procedures widely used in the corresponding fields. Moreover, in order to better understand the present invention, definitions and explanations of related terms are provided below. The term "antibody" mentioned here includes a whole antibody and any antigen-binding fragments (i.e., "antigen-binding portions") or single chains thereof "Antibody" refers to a glycoprotein comprising at least two heavy (H) chains and two light (L) chains connected to each other by disulfide bonds, or an antigen-binding portion thereof. Each heavy chain consists of a heavy chain variable region and a heavy chain constant region.

In the present invention, "homology" refers to the sequence similarity between two polynucleotide sequences or between two polypeptide sequences in the most preferred alignment.

The above description is only an overview of the technical solutions of the present invention. In order to understand the technical means of the present invention more clearly and implement it in accordance with the content of the disclosure, detailed description will be made below by way of preferred embodiments of the present invention and in conjunction with the accompanying drawings.

DETAILED DESCRIPTION OF THE INVENTION

Figure 1:
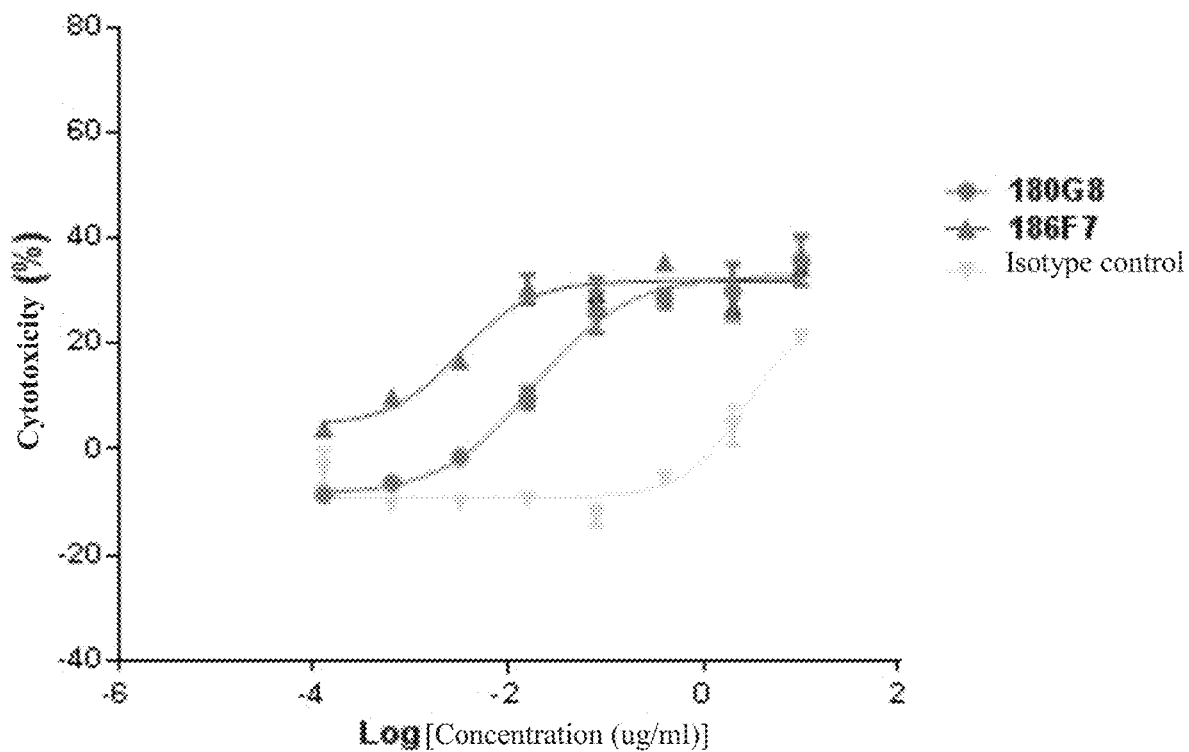
FIG. 1 shows the ADCC effect of humanized antibodies.

The present invention discloses a monoclonal antibody and its application. Those skilled in the art can learn from the content of the present disclosure to conduct the implementation by appropriately improving the process parameters. Particularly, it should be pointed out that all similar substitutions and modifications are obvious to those skilled in the art, and they are all deemed to be included in the present invention. The methods and applications of the present invention have been described in the preferred embodiments. It is obvious that relevant personnel can make changes or appropriate modifications and combinations to the methods and applications described herein without departing from the content and scope of the present invention, so as to implement and apply the technology of the present invention.

The monoclonal antibody provided by the present invention and the raw materials and reagents used in its application can be purchased from the market.

The present invention is further illustrated in conjunction with examples.

EXAMPLE

1. Preparation of Antigen
Preparation of GST-ECD Protein

The partial sequence of the first extracellular domain of human claudin 18.2 was constructed on the pGEX-KG vector (antigen sequence 1), and the constructed expression vector was transferred to the *E. coli* TG1 strain, and cultured in LB medium, and the antigen protein was expressed by the IPTG induction method. The collected *E. coli* TG1 cells were crushed with a homogenizer, affinity purified with Glutathione Sepharose 4 Fast Flow (GE, Cat #17-5132-01), and then subjected to secondary purification by the HiTrap Capto Q (GE, Cat #11001302) column, and the protein was dialyzed into PBS (pH 7.4), thus obtaining the antigen protein with a purity of more than 85%.

Preparation of DNA Immunogen

The partial sequence or full-length sequence of the first extracellular domain of claudin 18.2 was constructed on the pcDNA3.1 vector to function as an immunogen (antigen sequence 2, antigen sequence 3).

Stable Cell Line Construction of Human Claudin 18.1 and Human Claudin 18.2

The full-length sequences of human claudin 18.1 and human claudin 18.2 were cloned into pcDNA3.1(-) vector, and the constructed expression vector was transferred into HEK293F cells using Lipofectamine™ 3000 Transfection Reagent (Thermo, Cat #L3000150) reagent; the cells were screened with 400 μg/ml G418 (Gibco, Cat #10131-027); and after QPCR and FACS screening and verification, HEK293F_human claudin 18.1 and HEK293F_human claudin 18.2 cell lines with stable expression were obtained.

The full-length sequence of human claudin 18.2 was cloned into an adenovirus vector, and the constructed expression vector was transferred into CHO-K1 cells using Lipofectamine™ 3000 Transfection Reagent (Thermo, Cat #L3000150) reagent; the cells were screened with 5 μg/mL puromycin (Gibco, Cat #10131-027); and after Q-PCR and FACS screening and verification, CHO-K1_human claudin 18.2 cell line with stable expression was obtained.

2. Animal Immunity

In order to obtain high-affinity and high-specificity antibodies against human claudin 18.2, this experiment designed a series of antigen combinations (DNA immunity, protein immunity and cell line whole cell immunity) to immunize several Balb/c mice and C57BL/6 mice. The classical immunization schedule was used to immunize the mice, thereby promoting the immune response of the mice. The serum of the mice was collected, the serum titer was determined by the ELISA method using the GST-ECD protein cell line as the antigen, or by FACS using the CHO-K1 human claudin 18.2 cell line, and the corresponding mice with high titer were selected to enter the fusion.

3. Hybridoma Fusion and Screening

Before fusion, the SP2/0 status of mouse myeloma was adjusted to ensure that its growth density did not exceed 1×106, the animals were ultimately immunized 3 days in advance, and SP2/0 cells were fed one day in advance. With the plating number of 2.0×104 cells/well, the fusion was performed by an electrofusion instrument to ensure that the number ratio of splenocytes or lymph node cells to SP2/0 cells was between 10:1 and 5:1, and the number of splenocytes plated per well did not exceed 1×105; after 7 days of fusion, the supernatant was collected and the medium was replaced; the collected supernatant was tested by ELISA binding method and determined for the cell binding activity using a flow cytometer, thus obtaining hybridoma cell lines that were positive in 3 screening experiments.

A. ELISA Binding Method

GST-ECD was diluted with PBS (pH 7.4) coating solution to 0.5 μg/ml to coat a 96-well plate at a dose of 100 μl/well; after the 96-well plate was blocked, the hybridoma culture medium supernatant was added for incubation, after washing, Peroxidase-AffiniPure Goat Anti-Mouse IgG, Fcγ Fragment Specific (minX Hu, Bov, HrsSrProt) was added; after washing, the chromogenic substrate was added for incubation; and at the end of the reaction, the absorbance value of OD450 was read.

B. Cell ELISA Test

A 96-well plate was coated with CHO-K1_human claudin 18.2 cell line, with the plating number of 1×105 cells/well; after the 96-well plate was blocked, the primary antibody was a combination of hybridoma supernatant, a positive antibody, isotype control and PBS; after the primary antibody was incubated, the cell washing was conducted, Peroxidase-AffiniPure Goat Anti-Mouse IgG, Fcγ Fragment Specific (min X Hu, Bov, Hrs Sr Prot) was inoculated as a secondary antibody; after washing, the chromogenic substrate was added for incubation; and at the end of the reaction, the absorbance value of OD450 was read.

C. The Cell Binding Activity of Hybridoma Supernatant was Determined Using a Flow Cytometer.

The hybridoma supernatant was subjected to flow cytometric binding experiments on HEK293F_human claudin 18.1, HEK293F_human claudin 18.2 cell line and CHO-K1_human claudin 18.2 cell line, and the clone that specifically bound to human claudin 18.2 was the target clone.

50 μl of cells (2.5×105 cells/ml) were used for each reaction. The primary antibody was a combination of hybridoma supernatant, a positive antibody, isotype control and PBS; after the primary antibody was incubated, the cell washing was conducted, and Goat anti-Mouse IgG iFlour 647 (GenScript, 3 μg/ml) was used as a secondary antibody for incubation; after washing, a fluorescence signal was read by the flow cytometer.

4. Preparation and Activity Identification of Human-Mouse Chimeric Antibody

A. Acquisition of Murine Antibody Gene

The hybridoma cell line was extracted by Trizol (Ambion 15596-026) kit to extract the total RNA of hybridoma cells, and then the total RNA was reverse transcribed with Takara PrimeScript 1st Strand cDNA synthesis kit to prepare cDNA, and degenerate primers were used to amplify the heavy chain variable region sequence and the light chain variable region sequence of the antibody, respectively.

B. Construction of Human-Mouse Chimeric Antibody

The light chain variable region sequence of the mouse antibody was spliced with the human IgG kappa CL region sequence to obtain the full-length light chain sequence; and through full gene synthesis, the full-length light chain sequence was constructed on the pcDNA3.1 vector containing the nitrogen-terminal signal peptide to obtain the light chain expression vector.

The heavy chain variable region sequence of the mouse antibody was spliced with the CH1, CH2 and CH3 region sequences of human IgG4 S228P to obtain the full-length heavy chain sequence; and through full gene synthesis, the full-length heavy chain sequence was constructed on the pcDNA3.1 vector containing the nitrogen-terminal signal peptide to obtain the heavy chain expression vector.

C. Expression and Purification of Human-Mouse Chimeric Antibody

The light chain expression vector and the heavy chain expression vector were transiently transfected into HEK293F cells by co-transfection. The transfected 293F cells were cultured for 7 days, and the culture supernatant was collected. Then, the chimeric antibody in the supernatant was purified by a protein A affinity chromatography column and dialyzed into PBS (pH 7.4). The concentration was determined by A280 method and SDS-PAGE analysis was carried out.

D the Binding Ability of Human-Mouse Chimeric Antibody to Cells was Determined Using a Flow Cytometer.

The binding ability of human-mouse chimeric antibody to HEK293F_human claudin 18.1 and HEK293F_human claudin 18.2 cell lines was determined.

100 μl of cells (2.0×107 cells/ml) were used for each reaction. The primary antibody was a combination of a purified human-mouse chimeric antibody, a positive antibody (IMAB362 and Anti-Claudin18 antibody [34H14L15] (abcam, Cat #ab203563)), isotype control and 1% BSA in PBS; after the primary antibody was incubated, the cell washing was conducted, and Goat anti-human IgG Fc (FITC) (abcam, Cat #ab97224) and Goat Anti-Rabbit IgG H&L (Alexa Fluor® 488)(abcam, Cat #ab150077) was used as a secondary antibody for incubation; after washing, a fluorescence signal was read by the flow cytometer.

F. The Binding Ability of Human-Mouse Chimeric Antibody to Cancer Cell Line was Determined Using a Flow Cytometer.

100 μl of cells (1.0×107 cells/ml) were used for each reaction. The primary antibody was a combination of a human-mouse chimeric antibody, a positive antibody (IMAB362), isotype control and 1% BSA in PBS; after the primary antibody was incubated, the cell washing was conducted, and Goat anti-human IgG Fc (FITC) (abcam, Cat #ab97224) was used as a secondary antibody for incubation; after washing, a fluorescence signal was read by flow cytometer.

5. Humanization of Mouse Antibody

The variable region sequence of the mouse antibody was analyzed and aligned with human germline genes; the framework region sequence of the human light and heavy chain germline gene with the highest homology to the framework region sequence of the mouse antibody was selected as the basic skeleton, or specific amino acids in the framework region were selected for restoration mutations; then, the CDR region sequence of the mouse antibody was grafted with the framework region sequence of the selected human germline gene; after splicing, the light and heavy chain variable region sequences of the humanized antibody were respectively constructed on expression vectors including human IgG4 heavy chain Fc and human IgG kappa CL through gene synthesis. The constructed light and heavy chain vectors of the humanized antibody were paired with HEK293F for transient expression. After the antibody in the culture supernatant of the transient cells was affinity purified and dialyzed, the concentration was determined by A280 method and the concentration and purity were analyzed by SDSPAGE, and then FACS method was used to determine the affinity with HEK293F_human claudin 18.2 cell line.

6. ADCC Experiment of Antibody

The HEK293F_human claudin 18.2 cell line was used to determine the FPLC-purified humanized antibody of the invention to mediate complement-dependent cytotoxicity. The effector cells PBMC (including effector cells such as NK cells and monocytes) were derived from fresh blood samples provided by healthy blood donors. Fresh blood was diluted 4 times with DPBS (Gibco, 14190-144), and Ficoll-Paque Plus (GE, Healthcare) Density gradient centrifugation method was carried out to extract effector cell PBMC. The HEK293F_human claudin 18.2 cell line stably expressing CLDN18A2 was used as the target cell. The antibody to be tested and the control antibody were diluted with the medium (RPMI1640 medium (Gibco, 11835-030)+1% FBS (Gibco, 10099-141)) to a final concentration of 10 ug/ml, and then diluted 5 times for 8 gradients, and added to a 96-well cell U-shaped culture plate (Corning, 3799). The pre-diluted target cells (1E4 cells/well) were added to the 96-well culture plate at a dose of 40 µl/well. The diluted effector cells (2.5E5 cells/well) were added to the 96-well plate at a dose of 40 µl/well, and the ratio of effector cells:target cells was 25:1. The effector cells and the target cells were respectively added with culture medium as controls, mixed well, and incubated for 6 hours at 37° C. in the presence of 5% CO2. After the incubation, centrifugation was carried out at 1500 rpm/min (Eppendorf, 5810R) for 10 minutes. The supernatant was pipetted into a 96-well cell culture plate (Corning, 3599) at a dose of 70 µl/well. With use of LDH (Roche, 4744934001) kit, OD492/OD620 was tested by the multi-functional microplate reader (Thermo, MULTISKAN FC), and the percentage of cytotoxicity was calculated as follows: Cytotoxicity (%)=100*(OD sample−OD Target cell only-ODPBMC Only)/(OD Target cell lysis-OD Target cell only)*%.

7. CDC Experiment of Antibody

The HEK293F_human claudin 18.2 cell line stably expressing CLDN18A2 was used as the target cell. The antibody to be tested and the control antibody were diluted with the medium (RPMI1640 medium (Gibco, 11835-030)+ 1% FBS (Gibco, 10099-141)) to a final concentration of 50 ug/ml, and then diluted 5 times for 8 gradients, and the complement (Quidel, A113) was diluted to a final concentration of 1:50 (V/V). The pre-diluted antibody was added to a 96-well cell culture plate (Corning, 3917) at a dose of 40 µl/well. The pre-diluted target cells (1E4 cells/well) were added to the 96-well culture plate at a dose of 40 µl/well. The diluted complement was added to a 96-well plate at a dose of 40 µl/well. The effector cells and the complement were respectively added with culture medium as controls, mixed well, and incubated for 6 hours at 37° C. in the presence of 5% CO2. After the incubation, CellTiter-Glo® Luminescent Cell Viability Assay (Promega, G7571) was added to the 96-well cell culture plate at a dose of 50 µl/well. a multi-functional microplate reader (BioTek, Synergy 2) was used to test the chemiluminescence value, and the percentage of cytotoxicity was calculated as follows: Cytotoxicity (%)=100*(1−(RLU Sample−RLUPNHS)/(RLU Cell+ PNHS−RLUPNHS))*%.

8. Antigenic Epitope Mapping

The epitope mapping method of the antigen recognized by the antibody in the invention was carried out in accordance with the "epitope mapping method" disclosed in Johan Rockberg "Methods of Molecular Biology" (ISBN 978-1-4939-7839-7).

In short, the peptides of the overlapping peptide library for epitope mapping were designed according to the antigen sequence and synthesized at GenScript company, and the peptides were coated using a high-affinity ELISA plate; the peptides were first diluted with Na2CO3/NaHCO3 coating buffer (pH 9.59) and coated at 37° C. for about 2 hours, and the coating solution in the wells was discarded; then, the peptides diluted with PBS coating buffer (pH 7.4) were added into the wells and coated for the second time for 2 hours at 37° C., and the coating solution in the wells was discarded; and finally the polypeptides diluted with ddH2O were added into the wells and coated overnight at 4° C. for the third time. The polypeptides were washed with PBST containing 0.1% Tween-20 and the plate was blocked with 3% BSA/PBST. The antibody of the invention diluted with 0.5% BSA/PBST, a positive control, isotype, and 0.5% BSA/PBST were used as primary antibody, the primary antibody was incubated at 37° C. for 2 hours and washed with PBST containing 0.1% Tween-20; the goat anti-human Fc fragment antibody (Solarbio, Cat #SE101) coupled with the HRP group was diluted with 0.5% BSA/PBST to function as the secondary antibody, the secondary antibody was incubated at 37° C. for 1 hour and then washed with PBST containing 0.1% Tween-20; TMB substrate (Solarbio, Cat #PR1200) was added for coloration and the OD450 absorbance value was determined.

9. Species-Binding Characteristic and Affinity Assay of Humanized Antibodies

The species-binding characteristic of the humanized antibodies was tested by flow cytometry according to the method in Example 4. pcDNA3.1(+) vector was used to construct mouse, rat, rabbit and orangutan CLDN18A2 expression vectors, and ExpiFectamine™ 293 Transfection Kit (gibico, Cat #A14524) was used to transiently transfect the expression vectors into HEK293F cells, and samples were taken for assay 48 hours after the transfection. Flow cytometric analysis was carried out by using Blank HEK293F cells as negative controls and HEK293F cell lines stably expressing human CLDN18A1 and human CLDN18A2 as positive controls.

100 µl of cells (2.0×107 cells/ml) were used for each reaction. The primary antibody was a combination of the FPLC-purified humanized antibody of the invention, a positive antibody (IMAB362 and Anti-Claudin18 antibody [34H14L15] (abcam, Cat #ab203563)), isotype control and 1% BSA in PBS; after the primary antibody was incubated, the cell washing was conducted, and Goat anti-human IgG Fc (FITC) (abcam, Cat #ab97224) and Goat Anti-Rabbit IgG H&L (Alexa Fluor® 488)(abcam, Cat #ab150077) was used as a secondary antibody for incubation; after washing, a fluorescence signal was read by the flow cytometer.

10. Proliferation Inhibition

The HEK293F_human claudin 18.2 cell line stably expressing CLDN18A2 was used as the test cell. The antibody to be tested and the isotype control antibody were diluted with the medium (FreeStyle™ 293 Expression Medium (Gibco, 12338-018)) to a final concentration of 15 ug/ml, and then diluted 3.16 times for 8 gradients. The pre-diluted antibody was added to a 96-well cell culture plate (Corning, 3610) at a dose of 50 µl/well. The pre-diluted cells (5E3 cells/well) were added to the 96-well culture plate at a dose of 50 µl/well. After being mixed well, the mixture was incubated for 7 days at 37° C. in the presence of 5% CO2. After the incubation, CellTiter-Glo® Luminescent Cell Viability Assay (Promega, G7571) was added to the 96-well cell culture plate at a dose of 50 μl/well. a multi-functional microplate reader (BioTek, Synergy 2) was used to test the chemiluminescence value, and the percentage of cytotoxicity was calculated as follows: Cytotoxicity (%)=100*(RLUCell only−RLU Sample)/RLU Cell only*%.

Endocytosis

The HEK293F_human claudin 18.2 cell line stably expressing CLDN18A2 was used as the test cell. The antibody to be tested and the isotype control antibody the medium (FreeStyle™ 293 Expression Medium (Gibco, 12338-018)) were diluted to a concentration of 40 nM; 120 ul of Fab-ZAP (Advanced Targeting Systems, IT-51) and 120 uL of antibody or Saporin (Advanced Targeting Systems, PR-1) were mixed well, incubated at 37° C. for 1 hour in the presence of 5% CO2, and then diluted 2.5 times for 8 gradients. The pre-diluted antibody was added to a 96-well cell culture plate (Corning, 3610) at a dose of 50 μl/well. The pre-diluted target cells (5E3 cells/well) were added to the 96-well culture plate at a dose of 50 μl/well. After being mixed well, the mixture was incubated for 7 days at 37° C. in the presence of 5% CO2. After the incubation, CellTiter-Glo® Luminescent Cell Viability Assay (Promega, G7571) was added to the 96-well cell culture plate at a dose of 50 μl/well. A multifunctional microplate reader (BioTek, Synergy 2) was used to test the chemiluminescence value, a 4-parameter equation was used to fit the curve, and the chemiluminescence value Lum was used to make the antibody concentration graph or the percentage of cytotoxicity was calculated follows: Cytotoxicity (%)=100*(RLUCell only−RLU Sample)/RLU Cell only*%.

12. The Effect of Antibodies in Mouse Models

A. Treatment of Late-Onset Tumors with High Expression of CLDN18A2 in Mice 50 female BALB/c nude mice were subcutaneously inoculated with human gastric cancer cell NUGC-4 in the right axilla. When the tumor volume grew to an appropriate size, 36 tumor-bearing mice with tumor volume of 37.54-124.64 mm3 were selected and randomly divided into 6 groups: 1-Negative control group, 2-Positive control group (0.2 mg/mouse), 3-RB0011-FK-13 group (0.2 mg/mouse), 4-RB0011-FK-1 group (0.2 mg/mouse), 5-RB0011-FK-2 group (0.2 mg/mouse) and 6-186CG4-mut group (0.2 mg/mouse), 6 animals in each group, and then administered twice a week, intravenously for 4 weeks in total. General clinical observation was carried out twice a day after the first administration, weighing and measurement of the tumor diameter were carried out twice a week, the animals were euthanized on D29, and the tumor tissues were taken out and weighed to calculate the tumor volume, relative tumor volume (RTV) and relative tumor proliferation rate (T/C %).

Results

1. Preparation and Activity Identification of Human-Mouse Chimeric Antibody a. The Binding Ability of Human-Mouse Chimeric Antibody to Cells was Determined Using a Flow Cytometer.

One weakly positive clone (170B3) and two strong positive clones (180G8 and 186F7) were screened to specifically target HEK293F_human claudin 18.2.

TABLE 1

The binding of each clone to HEK293FJmman claudin 18.2

| Sample | MFI |
|---|---|
| First scanning | |
| Control | 1888 |
| 22C2 H1L1 | 1536 |
| 65F4 H1L1 | 1321 |
| 65F4 H1L3 | 2061 |
| 65F4 H2L1 | 1349 |
| 65F4 H2L2 | 1424 |
| 65F4 H3L2 | 2261 |
| 65F4 H3L3 | 1271 |
| 22C2 H2L1 | 1888 |
| Second scanning | |
| Control | 504 |
| 65F4 H2L3 | 628 |
| 65F4 H1L2 | 894 |
| Third scanning | |
| Control | 329 |
| 65F4 H3L1 | 406 |
| Fourth scanning | |
| Control | 309 |
| 22C2 H1L2 | 931 |
| 22C2 H2L2 | 317 |
| 170B3 H1L | 1009 |
| 172F1 | 1759 |
| 180G8 H1L1 | 424 |
| 180G8 H1L2 | 270 |
| 180G8 H1L3 | 270 |
| 180G8 H2L1 | 280 |
| 180G8 H2L2 | 293 |
| 180G8 H2L3 | 2790 |
| 180G8 H3L1 | 275 |
| 180G8 H3L2 | 462 |
| 180G8 H3L3 | 275 |
| 22C2 H3L1 | 353 |
| 22C2 H3L2 | 452 |
| 142C5 | 989 |
| I26D7 | 449 |
| 71B5 H1L | 297 |
| 71B5 H2L | 259 |
| 107C6 | 249 |
| 15F3 | 734 |
| Fifth scanning | |
| Control | 473 |
| 180GS H4L1 | 516 |
| 180GS H4L2 | 606 |
| 1S0GS H4L3 | 544 |
| 1S0GSH5L1 | 523 |
| 1S0GS H5L2 | 585 |
| 180G8H5L3 | 583 |
| Sixth scanning | |
| Control | 329 |
| 186F7 | 35069 |
| 170B3 H2L | 2021 |

TABLE 2

The binding of each clone to HEK293FJumian claudin18.2

| Sample | MFI |
|---|---|
| HEK293F_CLDN18.1 | |
| 170B3 H1L | 5158 |
| 170B3 H2L | 384 |
| 172F1 | 502 |

TABLE 2-continued

The binding of each clone to HEK293FJumian claudin18.2

| Sample | MFI |
|---|---|
| 22C2 H1L2 | 674 |
| 180G8 H2L3 | 358 |
| 142C5 | 1246 |
| 15F3 | 267 |
| 186F7 | 280 |
| HEK293F_CLDN18.2 | |
| 170B3 | 6928 |
| 170B3 H2L | 1151 |
| 172F1 | 749 |
| 22C2 H1L2 | 1195 |
| 180G8 H2L3 | 22934 |
| 142C5 | 1706 |
| 15F3 | 628 |
| 186F7 | 35069 |

Two strong positive clones (180G8 and 186F7) screened through the assay of the binding ability of human-mouse chimeric antibody to cancer cell lines by flow cytometer can bind to NUGC-4

| Antibody | Isotype control | 130GS | 186F7 |
|---|---|---|---|
| MF1 | 371 | 13300 | 10000 | c. The Affinity of Human-Mouse Chimeric Antibody to HEK293F_Human Claudin 18.2 Cell Line was Determined.

| Antibody | 170B3 | 180G8 | 186F7 |
|---|---|---|---|
| EC50(nM) | 1233 | 13.71 | 6659 |

2. ADCC Effect of Humanized Antibodies

The two humanized antibodies and HEK293F_human claudin 18.2 cell line showed ADCC effect, with EC50 of 0.019 μg/ml and 0.003 μg/ml, respectively. See FIG. 1

3. CDC Effect of Humanized Antibodies

Figure 2:
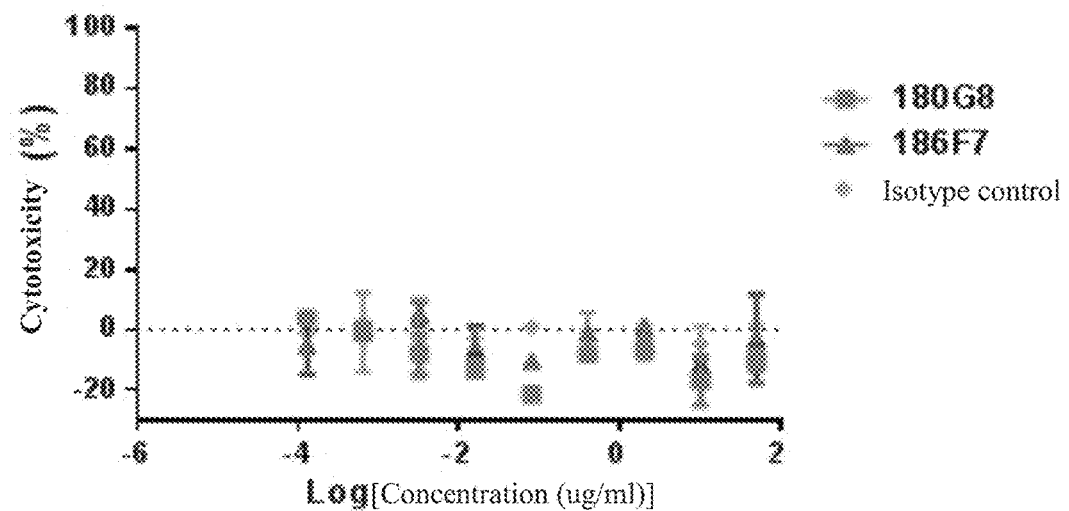
FIG. 2 shows the CDC effect of humanized antibodies.

The two humanized antibodies and HEK293F_human claudin 18.2 cell line did not show obvious CDC effect. See FIG. 2.

4. Antigenic Epitope Mapping

| | Polypeptide No. | MDQWSTQDLYNNPVT 1 | STQDLYNNPVTAVEN 2 | LYNNPVTAVENYQGL 3 | PVTAVFNYQGLWRSC 4 |
|---|---|---|---|---|---|
| Ab. 180G8 | No exchange | + | + | + | + |
| | Ser-Cys exchange | + | + | + | + |
| Ab 186F7 | No exchange | | + | | + |
| | Ser-Cys exchange | | + | | + |

| | Polypeptide No. | VFNYQGLWRSCVRES 5 | QGLWRSCVRESSGET 6 | RSCVRESSGFTECRG 7 |
|---|---|---|---|---|
| Ab. 180G8 | No exchange | + | | |
| | Ser-Cys exchange | + | | |
| Ab 186F7 | No exchange | + | | + |
| | Ser-Cys exchange | + | | |

5. Species-Binding Characteristic and Affinity Assay of Humanized Antibodies (EC50 (nM))

| Antibody | HEK293 | HEX293F_human CLDN18.1 | HEK293F_human CLDN18.2 | HEK293F_Mouse CLDN18.2 | HBK293F_Maca CLDN18.2 | HEK293F_Rat CLDN18.2 | HEK293F_Rabbit CLDN18.2 |
|---|---|---|---|---|---|---|---|
| Ab. 180G8 | NA | NA | 6.495 | 4.848 | 5.15 | 4,474 | 4.629 |
| Ab 186F7 | NA | NA | 7.012 | 7.106 | 8.265 | 6.473 | 5.995 | e. Proliferation Inhibition

Figure 3:
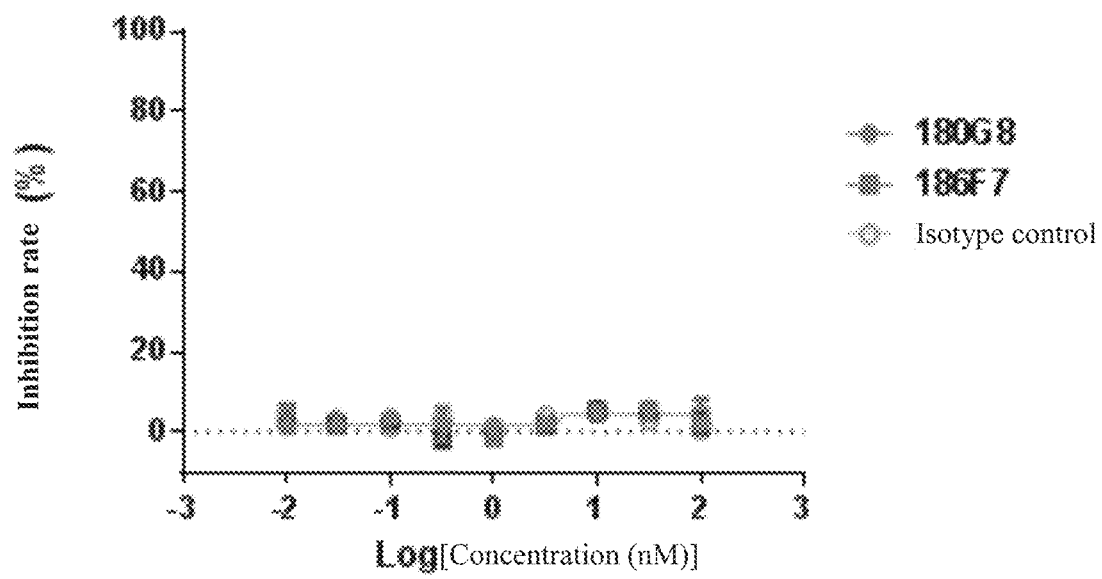
FIG. 3 shows the proliferation inhibition effect of humanized antibodies.

The two humanized antibodies showed no obvious proliferation inhibitory effect on the HEK293F_human claudin 18.2 cell line. See FIG. 3

6. Proliferation Inhibition

Figure 4:
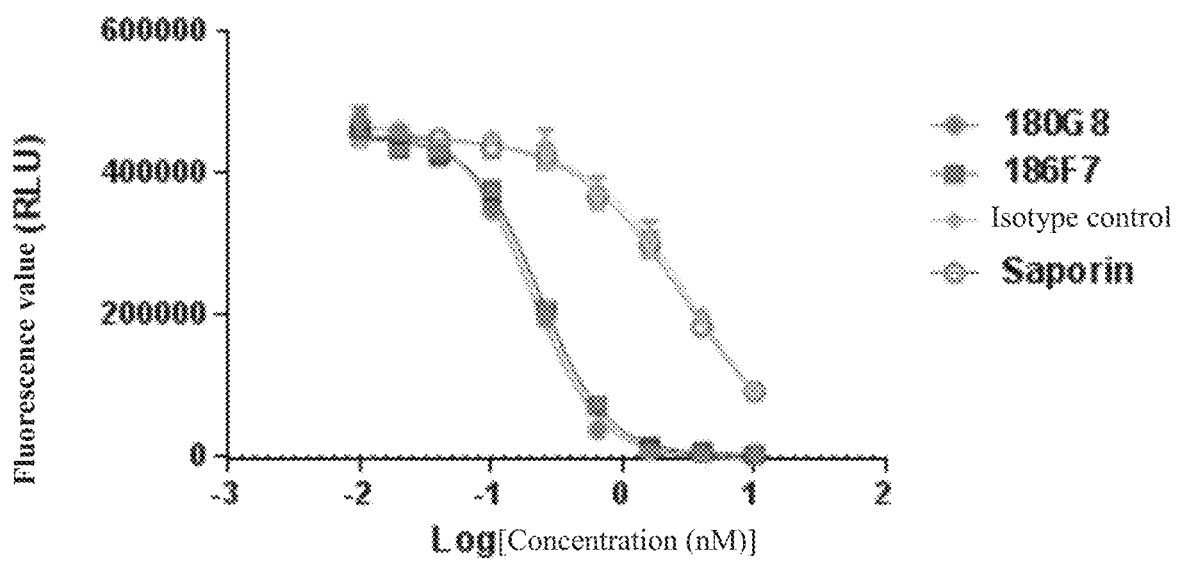
FIG. 4 shows the endocytosis effect of humanized antibodies.

The two humanized antibodies showed a certain endocytosis effect on the HEK293F_human claudin 18.2 cell line. See FIG. 4

Figure 5:
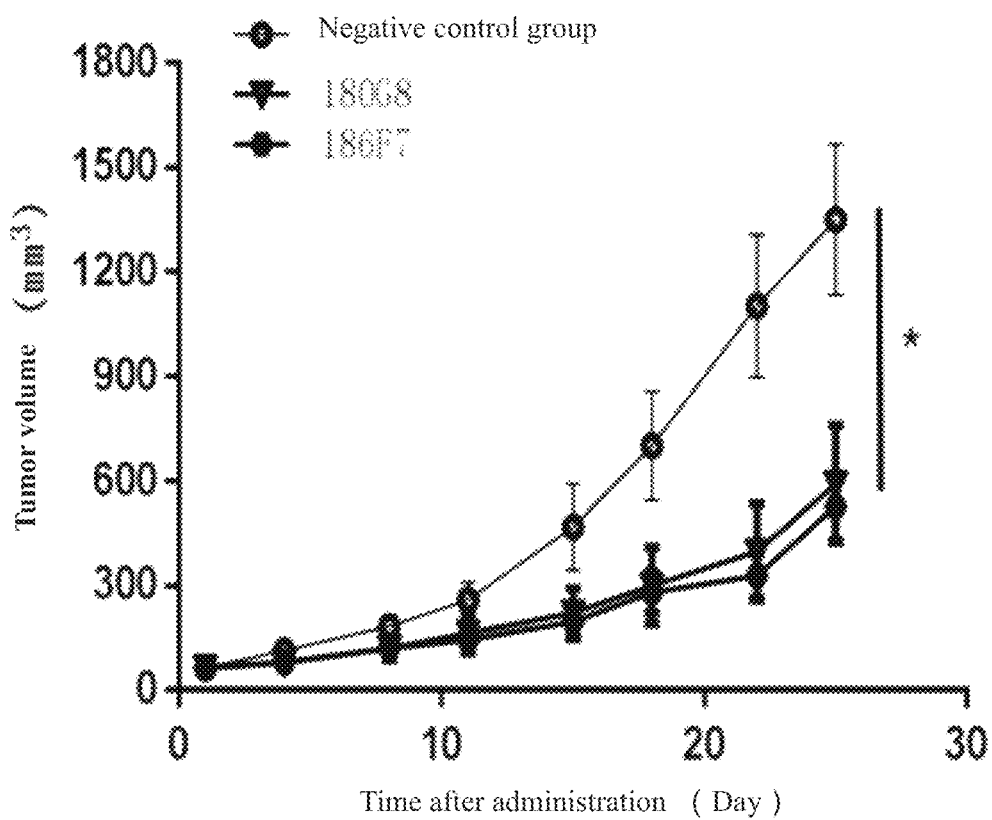
FIG. 5 is a graph showing the effect of antibodies in a mouse model.
Figure 6:
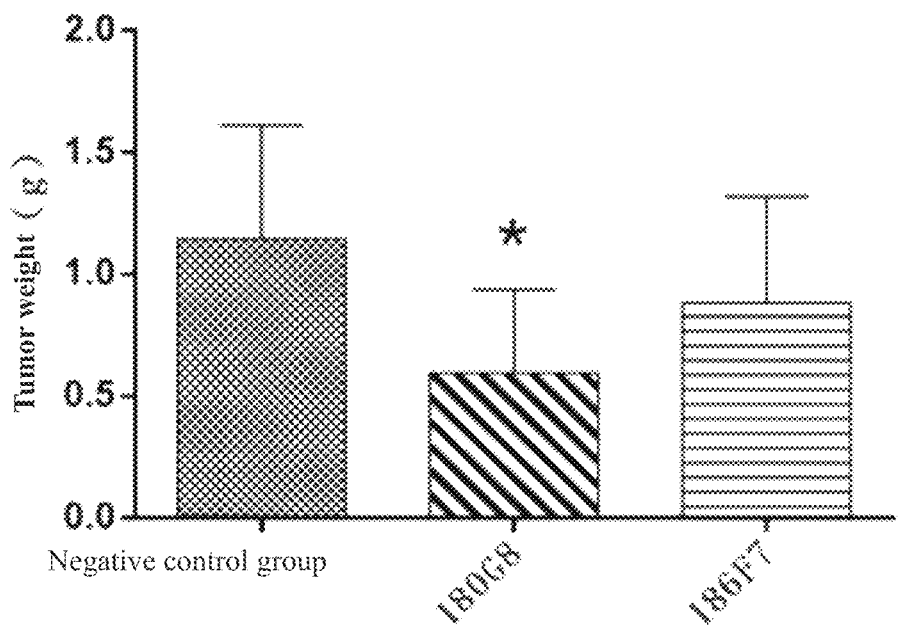
FIG. 6 is a histogram of the effect of antibodies in a mouse model.

7. The Effect of Antibodies in Mouse Models a. Treatment of Late-Onset Tumors with High Expression of CLDN18A2 in Mice This experiment successfully established a BALB/c subcutaneous xenograft tumor model in nude mice with human gastric cancer NUGC-4. Under the conditions of this experiment, the positive control and the test samples RB0011-FK-13, RB0011-FK-1, RB0011-FK-2 and 186CG4-mut were administered twice a week at a dose of 2 mg/mouse, for a total of 4 weeks of intravenous administration; they all showed an inhibitory effect on the growth of the BALB/c subcutaneous xenograft tumor nude mice with human gastric cancer NUGC-4. See FIG. 5 and FIG. 6.

What is claimed is:

1. An anti-human claudin 18.2 monoclonal antibody, having three heavy chain CDRs and three light chain CDRs, wherein
   a heavy chain CDR1 is SEQ ID NO: 1, a heavy chain CDR2 is SEQ ID NO: 2, a heavy chain CDR3 is SEQ ID NO: 3, a light chain CDR1 is SEQ ID NO: 4, a light chain CDR2 is SEQ ID NO: 5, and a light chain CDR3 is SEQ ID NO: 6; or
   a heavy chain CDR1 is SEQ ID NO: 7, a heavy chain CDR2 is SEQ ID NO: 8, a heavy chain CDR3 is SEQ ID NO: 9, a light chain CDR1 is SEQ ID NO: 10, a light chain CDR2 is SEQ ID NO: 11, a the light chain CDR3 is SEQ ID NO: 12; or
   a heavy chain CDR1 is SEQ ID NO: 13, a heavy chain CDR2 is SEQ ID NO: 14, a heavy chain CDR3 is SEQ ID NO: 15, a light chain CDR1 is SEQ ID NO: 16, a light chain CDR2 is SEQ ID NO: 17, a the light chain CDR3 is SEQ ID NO: 18; or
   a heavy chain CDR1 is SEQ ID NO: 19, a heavy chain CDR2 is SEQ ID NO: 20, a heavy chain CDR3 is SEQ ID NO: 21, a light chain CDR1 is SEQ ID NO: 22, a light chain CDR2 is SEQ ID NO: 23, and a light chain CDR3 is SEQ ID NO: 24; or
   a heavy chain CDR1 is SEQ ID NO: 25, a heavy chain CDR2 is SEQ ID NO: 26, a heavy chain CDR3 is SEQ ID NO: 27, a light chain CDR1 is SEQ ID NO: 28, a light chain CDR2 is SEQ ID NO: 29, a the light chain CDR3 is SEQ ID NO: 30.

2. The antibody according to claim 1, wherein:
   a heavy chain variable region comprises the heavy chain CDR1, the heavy chain CDR2 and the heavy chain CDR3; and
   a light chain variable region comprises the light chain CDR1, the light chain CDR2 and the light chain CDR3.

3. The antibody according to claim 2, wherein the amino acid sequence of the heavy chain variable region is SEQ ID NO: 79, and the amino acid sequence of the light chain variable region is SEQ ID NO: 80; or the amino acid sequence of the heavy chain variable region is SEQ ID NO: 81, and the amino acid sequence of the light chain variable region is SEQ ID NO: 82; or the amino acid sequence of the heavy chain variable region is SEQ ID NO: 83, and the amino acid sequence of the light chain variable region is SEQ ID NO: 84; or the amino acid sequence of the heavy chain variable region is SEQ ID NO: 85, and the amino acid sequence of the light chain variable region is SEQ ID NO: 86; or the amino acid sequence of the heavy chain variable region is SEQ ID NO: 87, and the amino acid sequence of the light chain variable region is SEQ ID NO: 88.

4. The antibody according to claim 1, wherein an amino acid sequence of a heavy chain comprises the heavy chain CDR1, the heavy chain CDR2, the heavy chain CDR3, the light chain CDR1, the light chain CDR2, and the light chain CDR3; the heavy chain CDR1 is SEQ ID NO: 1, the heavy chain CDR2 is SEQ ID NO: 2, the heavy chain CDR3 is SEQ ID NO: 3, the light chain CDR1 is SEQ ID NO: 4, the light chain CDR2 is SEQ ID NO: 5, and the light chain CDR3 is SEQ ID NO: 6; or the heavy chain CDR1 is SEQ ID NO: 7, the heavy chain CDR2 is SEQ ID NO: 8, the heavy chain CDR3 is SEQ ID NO: 9, the light chain CDR1 is SEQ ID NO: 10, the light chain CDR2 is SEQ ID NO: 11, and the light chain CDR3 is SEQ ID NO: 12; or the heavy chain CDR1 is SEQ ID NO: 13, the heavy chain CDR2 is SEQ ID NO: 14, the heavy chain CDR3 is SEQ ID NO: 15, the light chain CDR1 is SEQ ID NO: 16, the light chain CDR2 is SEQ ID NO: 17, and the light chain CDR3 is SEQ ID NO: 18; or the heavy chain CDR1 is SEQ ID NO: 19, the heavy chain CDR2 is SEQ ID NO: 20, the heavy chain CDR3 is SEQ ID NO: 21, the light chain CDR1 is SEQ ID NO: 22, the light chain CDR2 is SEQ ID NO: 23, and the light chain CDR3 is SEQ ID NO: 24; or the heavy chain CDR1 is SEQ ID NO: 25, the heavy chain CDR2 is SEQ ID NO: 26, the heavy chain CDR3 is SEQ ID NO: 27, the light chain CDR1 is SEQ ID NO: 28, the light chain CDR2 is SEQ ID NO: 29, and the light chain CDR3 is SEQ ID NO: 30.

5. A host cell, comprising the amino acid sequence of claim 1.

6. A conjugate, comprising the antibody of claim 1.

7. A composition, comprising a main component and an auxiliary component, wherein the main component comprises the antibody according to claim 1 or comprises a host cell containing the amino acid sequence of claim 1, or comprises a conjugate containing the antibody of claim 1; the auxiliary component is pharmaceutically acceptable carriers or excipients or other biologically active substances.

8. A kit, comprising the antibody of claim 1.

9. A nucleic acid molecule, comprising a nucleic acid sequence encoding the three heavy chain CDRs of the anti-human claudin 18.2 monoclonal antibody as described in claim 1, wherein the three heavy chain CDRs are as follows:

the heavy chain CDR1 is SEQ ID NO: 1, the heavy chain CDR2 is SEQ ID NO: 2 and the heavy chain CDR3 is SEQ ID NO: 3; or the heavy chain CDR1 is SEQ ID NO: 7, the heavy chain CDR2 is SEQ ID NO: 8 and the heavy chain CDR3 is SEQ ID NO: 9; or the heavy chain CDR1 is SEQ ID NO: 13, the heavy chain CDR2 is SEQ ID NO: 14 and the heavy chain CDR3 is SEQ ID NO: 15; or the heavy chain CDR1 is SEQ ID NO: 19, the heavy chain CDR2 is SEQ ID NO: 20 and the heavy chain CDR3 is SEQ ID NO: 21; or the heavy chain CDR1 is SEQ ID NO: 25, the heavy chain CDR2 is SEQ ID NO: 26 and the heavy chain CDR3 is SEQ ID NO: 27.

10. A vector, comprising the nucleic acid molecule according to claim 9.

11. A host cell, comprising the nucleic acid molecule of claim 9, or comprising a vector, the vector comprises the nucleic acid molecule of claim 9.

12. A composition, comprising a main component and an auxiliary component, wherein the main component comprises the nucleic acid molecule according to claim 9, or comprises a vector containing the nucleic acid molecule according to claim 9, or comprises a host cell containing the nucleic acid molecule according to claim 9, or comprises a host cell containing a vector which containing the nucleic acid molecule according to claim 9; the auxiliary component is pharmaceutically acceptable carriers or excipients or other biologically active substances.

\* \* \* \* \*

```
                        SEQUENCE LISTING

<160> NUMBER OF SEQ ID NOS: 104

<210> SEQ ID NO 1
    <211> LENGTH: 8
    <212> TYPE: PRT
    <213> ORGANISM: Artificial Sequence
    <220> FEATURE:
    <222> LOCATION: (1)..(8)
    <223> OTHER INFORMATION: Amino acid sequence of heavy chain CDR1

<400> SEQUENCE: 1

Gly Tyr Ala Phe Ser Ser Tyr Trp
    1               5

<210> SEQ ID NO 2
    <211> LENGTH: 9
    <212> TYPE: PRT
    <213> ORGANISM: Artificial Sequence
    <220> FEATURE:
    <222> LOCATION: (1)..(9)
    <223> OTHER INFORMATION: Amino acid sequence of heavy chain CDR2

<400> SEQUENCE: 2

Gln Ile Tyr Pro Gly Asp Ser Asn Thr
    1               5

<210> SEQ ID NO 3
    <211> LENGTH: 11
    <212> TYPE: PRT
    <213> ORGANISM: Artificial Sequence
    <220> FEATURE:
    <222> LOCATION: (1)..(11)
    <223> OTHER INFORMATION: Amino acid sequence of heavy chain CDR3

<400> SEQUENCE: 3

Ala Arg Ile Tyr Tyr Gly Asn Ser Phe Ala Tyr
    1               5                   10

<210> SEQ ID NO 4
    <211> LENGTH: 12
    <212> TYPE: PRT
    <213> ORGANISM: Artificial Sequence
    <220> FEATURE:
    <222> LOCATION: (1)..(12)
    <223> OTHER INFORMATION: Amino acid sequence of light chain CDR1

<400> SEQUENCE: 4

Gln Thr Leu Leu Asn Ser Gly Asn Gln Lys Asn Tyr
    1               5                   10

<210> SEQ ID NO 5
    <211> LENGTH: 6
    <212> TYPE: PRT
    <213> ORGANISM: Artificial Sequence
    <220> FEATURE:
    <222> LOCATION: (1)..(6)
```

-continued

```
<223> OTHER INFORMATION: Amino acid sequence of light chain CDR2

<400> SEQUENCE: 5

Trp Ala Ser Thr Arg Glu
1               5

<210> SEQ ID NO 6
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of light chain CDR3

<400> SEQUENCE: 6

Gln Asn Asp Tyr Phe Tyr Pro Phe Thr
1               5

<210> SEQ ID NO 7
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 7

Arg Phe Thr Leu Asn Ser Tyr Ala
1               5

<210> SEQ ID NO 8
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of heavy chain CDR2

<400> SEQUENCE: 8

Thr Ile Thr Ser Gly Val Ser His Thr
1               5

<210> SEQ ID NO 9
<211> LENGTH: 11
<212> TYPE: PRT
<213> ORGANISM: Artificial Sequence
<220> FEATURE:
<222> LOCATION: (1)..(11)
<223> OTHER INFORMATION: Amino acid sequence of heavy chain CDR3

<400> SEQUENCE: 9

Ala Arg Leu Tyr Tyr Gly Asn Ser Leu Asp Tyr
1               5                   10

<210> SEQ ID NO 10
<211> LENGTH: 12
<212> TYPE: PRT
<213> ORGANISM: Artificial Sequence
<220> FEATURE:
<222> LOCATION: (1)..(12)
<223> OTHER INFORMATION: Amino acid sequence of light chain CDR1

<400> SEQUENCE: 10

Gln Ser Leu Leu Asn Ser Gly Asn Gln Lys Asn Tyr
1               5                   10

<210> SEQ ID NO 11
```

```
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 11

Trp Ala Ser Thr Arg Glu
1               5

<210> SEQ ID NO 12
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of light chain CDR3

<400> SEQUENCE: 12

Gln Asn Asn Tyr Ile Tyr Pro Leu Thr
1               5

<210> SEQ ID NO 13
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 13

Gly Tyr Thr Phe Thr Glu Tyr Thr
1               5

<210> SEQ ID NO 14
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of heavy chain CDR2

<400> SEQUENCE: 14

Gly Ile Asn Pro Asn Asn Gly Gly Thr
1               5

<210> SEQ ID NO 15
<211> LENGTH: 11
<212> TYPE: PRT
<213> ORGANISM: Artificial Sequence
<220> FEATURE:
<222> LOCATION: (1)..(11)
<223> OTHER INFORMATION: Amino acid sequence of heavy chain CDR3

<400> SEQUENCE: 15

Ala Arg Trp Gly Lys Gly Gly Tyr Phe Asp Val
1               5                   10

<210> SEQ ID NO 16
<211> LENGTH: 10
<212> TYPE: PRT
<213> ORGANISM: Artificial Sequence
<220> FEATURE:
<222> LOCATION: (1)..(10)
<223> OTHER INFORMATION: Amino acid sequence of light chain CDR1

<400> SEQUENCE: 16
```

```
Lys Arg Val Ser Thr Ser Gly Tyr Ser Tyr
1               5                   10

<210> SEQ ID NO 17
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 17

Leu Thr Ser Asn Leu Glu
1               5

<210> SEQ ID NO 18
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of light chain CDR3

<400> SEQUENCE: 18

Gln His Ser Arg Glu Leu Pro Tyr Thr
1               5

<210> SEQ ID NO 19
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 19

Gly Phe Asn Ile Lys Asp Thr Tyr
1               5

<210> SEQ ID NO 20
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of heavy chain CDR2

<400> SEQUENCE: 20

Arg Ile Asp Pro Ala Asn Gly Asn Thr
1               5

<210> SEQ ID NO 21
<211> LENGTH: 11
<212> TYPE: PRT
<213> ORGANISM: Artificial Sequence
<220> FEATURE:
<222> LOCATION: (1)..(11)
<223> OTHER INFORMATION: Amino acid sequence of heavy chain CDR3

<400> SEQUENCE: 21

Ala Ser Leu Tyr Ser Tyr Gly Ala Met Asp Tyr
1               5                   10

<210> SEQ ID NO 22
<211> LENGTH: 5
<212> TYPE: PRT
<213> ORGANISM: Artificial Sequence
<220> FEATURE:
```

```
<222> LOCATION: (1)..(5)
<223> OTHER INFORMATION: Amino acid sequence of light chain CDR1

<400> SEQUENCE: 22

Ser Ser Ile Ser Tyr
1               5

<210> SEQ ID NO 23
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 23

Asp Thr Ser Lys Leu Ala
1               5

<210> SEQ ID NO 24
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of light chain CDR3

<400> SEQUENCE: 24

His Gln Arg Arg Ser Tyr Pro Tyr Thr
1               5

<210> SEQ ID NO 25
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 25

Gly Tyr Thr Phe Thr Asp Tyr Glu
1               5

<210> SEQ ID NO 26
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of heavy chain CDR2

<400> SEQUENCE: 26

Ala Ile Asp Pro Glu Thr Gly Gly Thr
1               5

<210> SEQ ID NO 27
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR3

<400> SEQUENCE: 27

Thr Gly Leu Trp Tyr Phe Asp Val
1               5
```

```
<210> SEQ ID NO 28
<211> LENGTH: 12
<212> TYPE: PRT
<213> ORGANISM: Artificial Sequence
<220> FEATURE:
<222> LOCATION: (1)..(12)
<223> OTHER INFORMATION: Amino acid sequence of light chain CDR1

<400> SEQUENCE: 28

Gln Ser Leu Leu Tyr Ser Ser Asn Gln Lys Asn Tyr
1               5                   10

<210> SEQ ID NO 29
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 29

Trp Ala Ser Thr Arg Glu
1               5

<210> SEQ ID NO 30
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of light chain CDR3

<400> SEQUENCE: 30

Gln Gln Tyr Tyr Ser Tyr Pro Tyr Thr
1               5

<210> SEQ ID NO 31
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 31

Gly Tyr Thr Phe Arg Gly Tyr Asp
1               5

<210> SEQ ID NO 32
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of heavy chain CDR2

<400> SEQUENCE: 32

Trp Ile Phe Pro Arg Asp Gly Ser Thr
1               5

<210> SEQ ID NO 33
<211> LENGTH: 15
<212> TYPE: PRT
<213> ORGANISM: Artificial Sequence
<220> FEATURE:
<222> LOCATION: (1)..(15)
<223> OTHER INFORMATION: Amino acid sequence of heavy chain CDR3

<400> SEQUENCE: 33
```

Ala Arg Asp Thr Asn Tyr Gly Ser Ser Pro Trp Tyr Phe Asp Val
1               5                   10                  15

<210> SEQ ID NO 34
<211> LENGTH: 11
<212> TYPE: PRT
<213> ORGANISM: Artificial Sequence
<220> FEATURE:
<222> LOCATION: (1)..(11)
<223> OTHER INFORMATION: Amino acid sequence of light chain CDR1

<400> SEQUENCE: 34

Gln Ser Leu Val His Ser Asn Gly Asn Thr Tyr
1               5                   10

<210> SEQ ID NO 35
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 35

Lys Val Ser Asp Arg Phe
1               5

<210> SEQ ID NO 36
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of light chain CDR3

<400> SEQUENCE: 36

Ser Gln Thr Thr His Ala Pro Phe Thr
1               5

<210> SEQ ID NO 37
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 37

Gly Tyr Thr Phe Thr Asp Tyr Tyr
1               5

<210> SEQ ID NO 38
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of heavy chain CDR2

<400> SEQUENCE: 38

Ile Phe Asn Pro Tyr Asn Gly Gly Ile
1               5

<210> SEQ ID NO 39
<211> LENGTH: 12
<212> TYPE: PRT
<213> ORGANISM: Artificial Sequence

```
<220> FEATURE:
<222> LOCATION: (1)..(12)
<223> OTHER INFORMATION: Amino acid sequence of heavy chain CDR3

<400> SEQUENCE: 39

Ala Arg Glu Asp Gly Asn Ser Gly Ala Met Asp Tyr
1               5                   10

<210> SEQ ID NO 40
<211> LENGTH: 11
<212> TYPE: PRT
<213> ORGANISM: Artificial Sequence
<220> FEATURE:
<222> LOCATION: (1)..(11)
<223> OTHER INFORMATION: Amino acid sequence of light chain CDR1

<400> SEQUENCE: 40

Gln Ser Leu Val His Ser Asn Gly Asn Thr Tyr
1               5                   10

<210> SEQ ID NO 41
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 41

Lys Val Ser Asp Arg Phe
1               5

<210> SEQ ID NO 42
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of light chain CDR3

<400> SEQUENCE: 42

Ser Gln Thr Thr His Ala Pro Phe Thr
1               5

<210> SEQ ID NO 43
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 43

Gly Asp Ser Ile Thr Ser Gly Tyr
1               5

<210> SEQ ID NO 44
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR2

<400> SEQUENCE: 44

Tyr Ile Ser Tyr Ser Gly Ser Thr
1               5
```

```
<210> SEQ ID NO 45
<211> LENGTH: 10
<212> TYPE: PRT
<213> ORGANISM: Artificial Sequence
<220> FEATURE:
<222> LOCATION: (1)..(10)
<223> OTHER INFORMATION: Amino acid sequence of heavy chain CDR3

<400> SEQUENCE: 45

Ala Arg Tyr Arg Tyr Tyr Ala Met Asp Tyr
1               5                   10

<210> SEQ ID NO 46
<211> LENGTH: 5
<212> TYPE: PRT
<213> ORGANISM: Artificial Sequence
<220> FEATURE:
<222> LOCATION: (1)..(5)
<223> OTHER INFORMATION: Amino acid sequence of light chain CDR1

<400> SEQUENCE: 46

Ser Ser Val Ser Tyr
1               5

<210> SEQ ID NO 47
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 47

Ser Thr Ser Asn Leu Ala
1               5

<210> SEQ ID NO 48
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of light chain CDR3

<400> SEQUENCE: 48

His Gln Trp Ser Ser Tyr Arg Thr
1               5

<210> SEQ ID NO 49
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 49

Gly Phe Ile Phe Ser Asn Tyr Glu
1               5

<210> SEQ ID NO 50
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of heavy chain CDR2
```

```
<400> SEQUENCE: 50

Ser Ile Ser Pro Ser Gly Gly Tyr Thr
1               5

<210> SEQ ID NO 51
<211> LENGTH: 10
<212> TYPE: PRT
<213> ORGANISM: Artificial Sequence
<220> FEATURE:
<222> LOCATION: (1)..(10)
<223> OTHER INFORMATION: Amino acid sequence of heavy chain CDR3

<400> SEQUENCE: 51

Thr Arg His Thr Ala Ser Tyr Phe Asp Tyr
1               5                   10

<210> SEQ ID NO 52
<211> LENGTH: 10
<212> TYPE: PRT
<213> ORGANISM: Artificial Sequence
<220> FEATURE:
<222> LOCATION: (1)..(10)
<223> OTHER INFORMATION: Amino acid sequence of light chain CDR1

<400> SEQUENCE: 52

Glu Ser Val Asp Asn Tyr Gly Ile Ser Phe
1               5                   10

<210> SEQ ID NO 53
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 53

Ala Ala Ser Asn Gln Gly
1               5

<210> SEQ ID NO 54
<211> LENGTH: 10
<212> TYPE: PRT
<213> ORGANISM: Artificial Sequence
<220> FEATURE:
<222> LOCATION: (1)..(10)
<223> OTHER INFORMATION: Amino acid sequence of light chain CDR3

<400> SEQUENCE: 54

Gln Gln Ser Lys Glu Val Pro Tyr Thr Phe
1               5                   10

<210> SEQ ID NO 55
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 55

Gly Phe Thr Phe Ser Asp Tyr Gly
1               5

<210> SEQ ID NO 56
<211> LENGTH: 9
<212> TYPE: PRT
```

```
<213> ORGANISM: Artificial Sequence
<220> FEATURE:
<222> LOCATION: (1)..(9)
<223> OTHER INFORMATION: Amino acid sequence of heavy chain CDR2

<400> SEQUENCE: 56

Tyr Ile Ser Ser Gly Ser Ser Thr Ile
1               5

<210> SEQ ID NO 57
<211> LENGTH: 13
<212> TYPE: PRT
<213> ORGANISM: Artificial Sequence
<220> FEATURE:
<222> LOCATION: (1)..(13)
<223> OTHER INFORMATION: Amino acid sequence of heavy chain CDR3

<400> SEQUENCE: 57

Ala Arg Gly Gly Phe Ile Thr Thr Val Gly Phe Ala Tyr
1               5                   10

<210> SEQ ID NO 58
<211> LENGTH: 10
<212> TYPE: PRT
<213> ORGANISM: Artificial Sequence
<220> FEATURE:
<222> LOCATION: (1)..(10)
<223> OTHER INFORMATION: Amino acid sequence of light chain CDR1

<400> SEQUENCE: 58

Glu Ser Val Asp Asn Tyr Gly Ile Ser Phe
1               5                   10

<210> SEQ ID NO 59
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 59

Ala Ala Ser Asn Gln Gly
1               5

<210> SEQ ID NO 60
<211> LENGTH: 10
<212> TYPE: PRT
<213> ORGANISM: Artificial Sequence
<220> FEATURE:
<222> LOCATION: (1)..(10)
<223> OTHER INFORMATION: Amino acid sequence of light chain CDR3

<400> SEQUENCE: 60

Gln Gln Ser Lys Glu Val Pro Tyr Thr Phe
1               5                   10

<210> SEQ ID NO 61
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 61

Gly Phe Ile Phe Ser Asn Tyr Glu
1               5
```

<210> SEQ ID NO 62
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of heavy chain CDR2

<400> SEQUENCE: 62

Ser Ile Ser Pro Ser Gly Gly Asn Thr
1               5

<210> SEQ ID NO 63
<211> LENGTH: 10
<212> TYPE: PRT
<213> ORGANISM: Artificial Sequence
<220> FEATURE:
<222> LOCATION: (1)..(10)
<223> OTHER INFORMATION: Amino acid sequence of heavy chain CDR3

<400> SEQUENCE: 63

Thr Arg His Thr Ala Ser Tyr Phe Asp Tyr
1               5                   10

<210> SEQ ID NO 64
<211> LENGTH: 11
<212> TYPE: PRT
<213> ORGANISM: Artificial Sequence
<220> FEATURE:
<222> LOCATION: (1)..(11)
<223> OTHER INFORMATION: Amino acid sequence of light chain CDR1

<400> SEQUENCE: 64

Gln Ser Leu Val His Ser Asn Gly Asn Thr Tyr
1               5                   10

<210> SEQ ID NO 65
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 65

Lys Val Ser Asn Arg Phe
1               5

<210> SEQ ID NO 66
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of light chain CDR3

<400> SEQUENCE: 66

Ser Gln Ser Thr His Val Leu Thr
1               5

<210> SEQ ID NO 67
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 67

Gly Phe Thr Phe Ser Asp Tyr Gly
1               5

<210> SEQ ID NO 68
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of heavy chain CDR2

<400> SEQUENCE: 68

Tyr Ile Ser Ser Gly Ser Ser Thr Ile
1               5

<210> SEQ ID NO 69
<211> LENGTH: 13
<212> TYPE: PRT
<213> ORGANISM: Artificial Sequence
<220> FEATURE:
<222> LOCATION: (1)..(13)
<223> OTHER INFORMATION: Amino acid sequence of heavy chain CDR3

<400> SEQUENCE: 69

Ala Arg Gly Gly Phe Ile Thr Thr Val Gly Phe Ala Tyr
1               5                   10

<210> SEQ ID NO 70
<211> LENGTH: 11
<212> TYPE: PRT
<213> ORGANISM: Artificial Sequence
<220> FEATURE:
<222> LOCATION: (1)..(11)
<223> OTHER INFORMATION: Amino acid sequence of light chain CDR1

<400> SEQUENCE: 70

Gln Ser Leu Leu Tyr Ser Asn Gly Lys Thr Tyr
1               5                   10

<210> SEQ ID NO 71
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 71

Leu Val Ser Lys Leu Asp
1               5

<210> SEQ ID NO 72
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of light chain CDR3

<400> SEQUENCE: 72

Val Gln Gly Thr His Phe Pro Phe Thr
1               5

<210> SEQ ID NO 73
<211> LENGTH: 8

```
<212> TYPE: PRT
<213> ORGANISM: Artificial Sequence
<220> FEATURE:
<222> LOCATION: (1)..(8)
<223> OTHER INFORMATION: Amino acid sequence of heavy chain CDR1

<400> SEQUENCE: 73

Gly Tyr Thr Phe Thr Asp Tyr Asn
1               5

<210> SEQ ID NO 74
<211> LENGTH: 9
<212> TYPE: PRT
<213> ORGANISM: Artificial Sequence
<220> FEATURE:
<222> LOCATION: (1)..(9)
<223> OTHER INFORMATION: Amino acid sequence of heavy chain CDR2

<400> SEQUENCE: 74

Asp Ile Asn Pro Asn Asn Gly Gly Thr
1               5

<210> SEQ ID NO 75
<211> LENGTH: 11
<212> TYPE: PRT
<213> ORGANISM: Artificial Sequence
<220> FEATURE:
<222> LOCATION: (1)..(11)
<223> OTHER INFORMATION: Amino acid sequence of heavy chain CDR3

<400> SEQUENCE: 75

Ala Arg Phe Arg Val Tyr Tyr Ala Met Asp Tyr
1               5                   10

<210> SEQ ID NO 76
<211> LENGTH: 11
<212> TYPE: PRT
<213> ORGANISM: Artificial Sequence
<220> FEATURE:
<222> LOCATION: (1)..(11)
<223> OTHER INFORMATION: Amino acid sequence of light chain CDR1

<400> SEQUENCE: 76

Gln Ser Leu Val His Ser Asn Gly Asn Thr Tyr
1               5                   10

<210> SEQ ID NO 77
<211> LENGTH: 6
<212> TYPE: PRT
<213> ORGANISM: Artificial Sequence
<220> FEATURE:
<222> LOCATION: (1)..(6)
<223> OTHER INFORMATION: Amino acid sequence of light chain CDR2

<400> SEQUENCE: 77

Lys Val Ser Asn Arg Phe
1               5

<210> SEQ ID NO 78
<211> LENGTH: 8
<212> TYPE: PRT
<213> ORGANISM: Artificial Sequence
<220> FEATURE:
<222> LOCATION: (1)..(8)
<223> OTHER INFORMATION: Amino acid sequence of light chain CDR3

<400> SEQUENCE: 78

Ser Gln Ser Thr His Val Leu Thr
```

<210> SEQ ID NO 79
<211> LENGTH: 119
<212> TYPE: PRT
<213> ORGANISM: Artificial Sequence
<220> FEATURE:
<222> LOCATION: (1)..(119)
<223> OTHER INFORMATION: Amino acid sequence of heavy chain variable
      region

<400> SEQUENCE: 79

Gln Val Gln Leu Gln Gln Ser Gly Ala Glu Leu Ala Lys Pro Gly Ala
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Lys Gly Leu Glu Trp Ile
            35                  40                  45

Gly Gln Ile Tyr Pro Gly Asp Ser Asn Thr Asn Tyr Asn Gly Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ile Tyr Tyr Gly Asn Ser Phe Ala Tyr Trp Gly Gln Gly Thr
                100                 105                 110

Leu Val Ile Val Ser Ala Ser
        115

<210> SEQ ID NO 80
<211> LENGTH: 113
<212> TYPE: PRT
<213> ORGANISM: Artificial Sequence
<220> FEATURE:
<222> LOCATION: (1)..(113)
<223> OTHER INFORMATION: Amino acid sequence of light chain variable
      region

<400> SEQUENCE: 80

Asp Ile Val Met Thr Gln Ser Pro Ser Phe Leu Thr Val Thr Thr Gly
1               5                   10                  15

Glu Arg Val Thr Met Ser Cys Lys Ser Ser Gln Thr Leu Leu Asn Ser
                20                  25                  30

Gly Asn Gln Lys Asn Tyr Leu Thr Trp Tyr Gln Gln Arg Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Phe Tyr Pro Phe Thr Phe Gly Gly Gly Thr Lys Leu Glu Ile
                100                 105                 110

Lys

<210> SEQ ID NO 81
<211> LENGTH: 118
<212> TYPE: PRT
<213> ORGANISM: Artificial Sequence
<220> FEATURE:

```
<222> LOCATION: (1)..(118)
<223> OTHER INFORMATION: Amino acid sequence of heavy chain variable
      region

<400> SEQUENCE: 81

Glu Val Met Leu Val Glu Ser Gly Gly Gly Leu Val Lys Pro Gly Gly
1               5                   10                  15

Ser Leu Lys Leu Ser Cys Ala Ala Ser Arg Phe Thr Leu Asn Ser Tyr
            20                  25                  30

Ala Met Ser Trp Ile Arg Gln Thr Pro Glu Lys Lys Leu Glu Trp Val
        35                  40                  45

Ala Thr Ile Thr Ser Gly Val Ser His Thr Tyr Tyr Phe Asp Ser Val
    50                  55                  60

Lys Gly Arg Phe Thr Ile Ser Arg Asp Thr Ala Lys Asn Thr Leu Asn
65                  70                  75                  80

Leu Gln Met Asn Ser Leu Arg Ser Glu Asp Thr Ala Val Tyr Tyr Cys
                85                  90                  95

Ala Arg Leu Tyr Tyr Gly Asn Ser Leu Asp Tyr Trp Gly Gln Gly Thr
            100                 105                 110

Ser Val Thr Val Ser Ser
            115

<210> SEQ ID NO 82
<211> LENGTH: 113
<212> TYPE: PRT
<213> ORGANISM: Artificial Sequence
<220> FEATURE:
<222> LOCATION: (1)..(113)
<223> OTHER INFORMATION: Amino acid sequence of light chain variable
      region

<400> SEQUENCE: 82

Asp Ile Val Met Thr Gln Ser Pro Ser Ser Leu Thr Val Thr Ala Gly
1               5                   10                  15

Glu Lys Val Thr Val Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ser Glu Asp Leu Ala Val Tyr Tyr Cys Gln Asn
                85                  90                  95

Asn Tyr Ile Tyr Pro Leu Thr Phe Gly Ala Gly Thr Thr Leu Glu Leu
            100                 105                 110

Lys

<210> SEQ ID NO 83
<211> LENGTH: 118
<212> TYPE: PRT
<213> ORGANISM: Artificial Sequence
<220> FEATURE:
<222> LOCATION: (1)..(118)
<223> OTHER INFORMATION: Amino acid sequence of heavy chain variable
      region

<400> SEQUENCE: 83

Glu Val Gln Leu Gln Gln Ser Gly Pro Glu Leu Val Lys Pro Gly Ala
1               5                   10                  15
```

```
Ser Val Lys Ile Ser Cys Lys Thr Ser Gly Tyr Thr Phe Thr Glu Tyr
         20                  25                  30

Thr Met His Trp Val Lys Gln Ser His Gly Lys Ser Leu Glu Trp Ile
         35                  40                  45

Gly Gly Ile Asn Pro Asn Asn Gly Gly Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Ile Arg Ser Leu Thr Ser Glu Asp Ser Ala Val Tyr Tyr Cys
             85                  90                  95

Ala Arg Trp Gly Lys Gly Gly Tyr Phe Asp Val Trp Gly Ala Gly Thr
                100                 105                 110

Thr Val Thr Val Ser Ser
        115
```

<210> SEQ ID NO 84
<211> LENGTH: 112
<212> TYPE: PRT
<213> ORGANISM: Artificial Sequence
<220> FEATURE:
<222> LOCATION: (1)..(112)
<223> OTHER INFORMATION: Amino acid sequence of light chain variable
      region

<400> SEQUENCE: 84

```
Asp Ile Val Leu Thr Gln Ser Pro Ala Ser Leu Gly Val Ser Leu Gly
 1               5                  10                  15

Gln Arg Ala Thr Ile Ser Cys Arg Ala Ser Lys Arg Val Ser Thr Ser
             20                  25                  30

Gly Tyr Ser Tyr Met His Trp Tyr Gln Gln Lys Pro Gly Gln Pro Pro
         35                  40                  45

Lys Leu Leu Ile Tyr Leu Thr Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
             85                  90                  95

Glu Leu Pro Tyr Thr Phe Gly Gly Gly Thr Lys Leu Glu Ile Lys Arg
                100                 105                 110
```

<210> SEQ ID NO 85
<211> LENGTH: 118
<212> TYPE: PRT
<213> ORGANISM: Artificial Sequence
<220> FEATURE:
<222> LOCATION: (1)..(118)
<223> OTHER INFORMATION: Amino acid sequence of heavy chain variable
      region

<400> SEQUENCE: 85

```
Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
             20                  25                  30

Tyr Met His Trp Val Lys Gln Arg Pro Glu Gln Gly Leu Glu Trp Ile
         35                  40                  45

Gly Arg Ile Asp Pro Ala Asn Gly Asn Thr Lys Tyr Asp Pro Lys Phe
 50                  55                  60
```

```
Gln Gly Lys Ala Thr Ile Thr Ala Asp Thr Ser Asn Thr Ala Tyr
65                  70                  75                  80

Leu His Leu Ser Ser Leu Thr Ser Glu Asp Thr Ala Val Tyr Cys Cys
                85                  90                  95

Ala Ser Leu Tyr Ser Tyr Gly Ala Met Asp Tyr Trp Gly Gln Gly Thr
            100                 105                 110

Ser Val Thr Val Ser Ser
        115

<210> SEQ ID NO 86
<211> LENGTH: 107
<212> TYPE: PRT
<213> ORGANISM: Artificial Sequence
<220> FEATURE:
<222> LOCATION: (1)..(107)
<223> OTHER INFORMATION: Amino acid sequence of light chain variable
      region

<400> SEQUENCE: 86

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Arg Ser Tyr Pro Tyr Thr
                85                  90                  95

Phe Gly Gly Gly Thr Lys Leu Glu Ile Lys Arg
            100                 105

<210> SEQ ID NO 87
<211> LENGTH: 114
<212> TYPE: PRT
<213> ORGANISM: Artificial Sequence
<220> FEATURE:
<222> LOCATION: (1)..(114)
<223> OTHER INFORMATION: Amino acid sequence of heavy chain variable
      region

<400> SEQUENCE: 87

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Leu Trp Tyr Phe Asp Val Trp Gly Thr Gly Thr Thr Val Thr
            100                 105                 110

Val Ser
```

<210> SEQ ID NO 88
<211> LENGTH: 114
<212> TYPE: PRT
<213> ORGANISM: Artificial Sequence
<220> FEATURE:
<222> LOCATION: (1)..(114)
<223> OTHER INFORMATION: Amino acid sequence of light chain variable region

<400> SEQUENCE: 88

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys Arg

<210> SEQ ID NO 89
<211> LENGTH: 122
<212> TYPE: PRT
<213> ORGANISM: Artificial Sequence
<220> FEATURE:
<222> LOCATION: (1)..(122)
<223> OTHER INFORMATION: Amino acid sequence of heavy chain variable region

<400> SEQUENCE: 89

Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Arg Gly Tyr
            20                  25                  30

Asp Ile Asn Trp Val Lys Gln Arg Pro Gly Gln Gly Leu Glu Trp Ile
        35                  40                  45

Gly Trp Ile Phe Pro Arg Asp Gly Ser Thr Lys Tyr Asn Glu Asn Phe
    50                  55                  60

Lys Asp Lys Ala Thr Leu Thr Val Asp Thr Ser Ser Asn Thr Ala Tyr
65                  70                  75                  80

Met Glu Phe His Ser Leu Thr Ser Glu Asp Ser Ala Val Tyr Phe Cys
                85                  90                  95

Ala Arg Asp Thr Asn Tyr Gly Ser Ser Pro Tyr Phe Asp Val Trp
            100                 105                 110

Gly Ala Gly Thr Ala Val Thr Val Ser Ser
        115                 120

<210> SEQ ID NO 90
<211> LENGTH: 113
<212> TYPE: PRT
<213> ORGANISM: Artificial Sequence
<220> FEATURE:
<222> LOCATION: (1)..(113)

```
<223> OTHER INFORMATION: Amino acid sequence of light chain variable
      region

<400> SEQUENCE: 90

Asp Val Val Met Thr Gln Ile Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asp Arg Phe Ser Gly Val Pro
    50                  55                  60

Asp Arg Phe Ser Gly Ser Lys Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Ala Pro Phe Thr Phe Gly Ser Gly Thr Lys Leu Glu Ile Lys
            100                 105                 110

Arg

<210> SEQ ID NO 91
<211> LENGTH: 119
<212> TYPE: PRT
<213> ORGANISM: Artificial Sequence
<220> FEATURE:
<222> LOCATION: (1)..(119)
<223> OTHER INFORMATION: Amino acid sequence of heavy chain variable
      region

<400> SEQUENCE: 91

Gln Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Ile Phe Asn Pro Tyr Asn Gly Gly Ile Ser Tyr Asn Gln Lys Phe
    50                  55                  60

Arg Gly Lys Ala Thr Leu Thr Val Asp Lys Ser Ser Asn Thr Ala Tyr
65                  70                  75                  80

Met Asp Leu Asn Ser Leu Thr Ser Glu Asp Ser Ala Val Tyr Tyr Cys
                85                  90                  95

Ala Arg Glu Asp Gly Asn Ser Gly Ala Met Asp Tyr Trp Gly Gln Gly
            100                 105                 110

Thr Ser Leu Thr Val Ser Ser
        115

<210> SEQ ID NO 92
<211> LENGTH: 113
<212> TYPE: PRT
<213> ORGANISM: Artificial Sequence
<220> FEATURE:
<222> LOCATION: (1)..(113)
<223> OTHER INFORMATION: Amino acid sequence of light chain variable
      region

<400> SEQUENCE: 92

Asp Val Val Met Thr Gln Ile Pro Phe Ser Leu Pro Val Ser Leu Gly
1               5                   10                  15
```

```
Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asp Arg Phe Ser Gly Val Pro
        50                  55                  60

Asp Arg Phe Ser Gly Ser Lys Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Ala Pro Phe Thr Phe Gly Ser Gly Thr Lys Leu Glu Ile Lys
            100                 105                 110

Arg

<210> SEQ ID NO 93
<211> LENGTH: 116
<212> TYPE: PRT
<213> ORGANISM: Artificial Sequence
<220> FEATURE:
<222> LOCATION: (1)..(116)
<223> OTHER INFORMATION: Amino acid sequence of heavy chain variable
      region

<400> SEQUENCE: 93

Gln Val Gln Leu Lys Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
            35                  40                  45

Gly Tyr Ile Ser Tyr Ser Gly Ser Thr Tyr Tyr Asn Pro Ser Leu Lys
        50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Arg Tyr Tyr Ala Met Asp Tyr Trp Gly Gln Gly Thr Ser Val
            100                 105                 110

Thr Val Ser Ser
            115

<210> SEQ ID NO 94
<211> LENGTH: 106
<212> TYPE: PRT
<213> ORGANISM: Artificial Sequence
<220> FEATURE:
<222> LOCATION: (1)..(106)
<223> OTHER INFORMATION: Amino acid sequence of light chain variable
      region

<400> SEQUENCE: 94

Asp Ile Glu Leu Thr Gln Ser Pro Ala Ile Met Ser Ala Ser Leu Gly
1               5                   10                  15

Glu Glu Ile Thr Leu Thr Cys Ser Ala Ser Ser Ser Val Ser Tyr Met
            20                  25                  30

His Trp Tyr Gln Gln Lys Ser Gly Thr Ser Pro Lys Leu Leu Ile Tyr
            35                  40                  45

Ser Thr Ser Asn Leu Ala Ser Gly Val Pro Ser Arg Phe Ser Gly Ser
        50                  55                  60
```

```
Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Ser Tyr Arg Thr Phe
                85                  90                  95

Gly Gly Gly Thr Lys Leu Glu Ile Lys Arg
            100                 105

<210> SEQ ID NO 95
<211> LENGTH: 117
<212> TYPE: PRT
<213> ORGANISM: Artificial Sequence
<220> FEATURE:
<222> LOCATION: (1)..(117)
<223> OTHER INFORMATION: Amino acid sequence of heavy chain variable
      region

<400> SEQUENCE: 95

Asp Val Leu Leu Val Glu Ser Gly Gly Gly Leu Val Gln Pro Gly Arg
1               5                   10                  15

Ser Leu Lys Leu Ser Cys Glu Val Ser Gly Phe Ile Phe Ser Asn Tyr
                20                  25                  30

Glu Met Ala Trp Val Arg Gln Ala Pro Thr Lys Gly Leu Glu Trp Val
            35                  40                  45

Ala Ser Ile Ser Pro Ser Gly Gly Tyr Thr Ser Tyr Arg Asp Ser Val
        50                  55                  60

Lys Gly Arg Phe Thr Val Ser Arg Asp Asn Ala Lys Thr Asn Leu Tyr
65                  70                  75                  80

Leu Gln Met Asp Ser Leu Arg Ser Glu Asp Thr Ala Thr Tyr Tyr Cys
                85                  90                  95

Thr Arg His Thr Ala Ser Tyr Phe Asp Tyr Trp Gly Gln Gly Val Met
            100                 105                 110

Val Thr Val Ser Ser
            115

<210> SEQ ID NO 96
<211> LENGTH: 112
<212> TYPE: PRT
<213> ORGANISM: Artificial Sequence
<220> FEATURE:
<222> LOCATION: (1)..(112)
<223> OTHER INFORMATION: Amino acid sequence of light chain variable
      region

<400> SEQUENCE: 96

Asp Ile Glu Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly Ile Ser Phe Met Asn Trp Phe Gln Gln Lys Pro Gly Gln Pro Pro
            35                  40                  45

Lys Leu Leu Ile Tyr Ala Ala Ser Asn Gln Gly Ser Gly Val Pro Ala
        50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Tyr Thr Phe Gly Gly Gly Thr Lys Leu Glu Ile Lys Arg
            100                 105                 110
```

```
<210> SEQ ID NO 97
<211> LENGTH: 120
<212> TYPE: PRT
<213> ORGANISM: Artificial Sequence
<220> FEATURE:
<222> LOCATION: (1)..(120)
<223> OTHER INFORMATION: Amino acid sequence of heavy chain variable
      region

<400> SEQUENCE: 97

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Gly Phe Ile Thr Thr Val Gly Phe Ala Tyr Trp Gly Gln
            100                 105                 110

Gly Thr Leu Val Thr Val Ser Ala
            115                 120

<210> SEQ ID NO 98
<211> LENGTH: 112
<212> TYPE: PRT
<213> ORGANISM: Artificial Sequence
<220> FEATURE:
<222> LOCATION: (1)..(112)
<223> OTHER INFORMATION: Amino acid sequence of light chain variable
      region

<400> SEQUENCE: 98

Asp Ile Glu Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Tyr Thr Phe Gly Gly Gly Thr Lys Leu Glu Ile Lys Arg
            100                 105                 110

<210> SEQ ID NO 99
<211> LENGTH: 117
<212> TYPE: PRT
<213> ORGANISM: Artificial Sequence
<220> FEATURE:
<222> LOCATION: (1)..(117)
<223> OTHER INFORMATION: Amino acid sequence of heavy chain variable
      region
```

<400> SEQUENCE: 99

Glu Val Leu Leu Val Glu Ser Gly Gly Gly Leu Val Gln Pro Gly Arg
1               5                   10                  15

Ser Leu Lys Leu Ser Cys Glu Val Ser Gly Phe Ile Phe Ser Asn Tyr
            20                  25                  30

Glu Met Ala Trp Val Arg Gln Ala Pro Thr Lys Gly Leu Glu Trp Val
        35                  40                  45

Ala Ser Ile Ser Pro Ser Gly Gly Asn Thr Tyr Tyr Arg Asp Ser Val
    50                  55                  60

Lys Gly Arg Phe Thr Val Ser Arg Asp Asn Ala Lys Thr Asn Leu Tyr
65                  70                  75                  80

Leu Gln Met Asp Ser Leu Arg Ser Glu Asp Thr Ala Thr Tyr Tyr Cys
            85                  90                  95

Thr Arg His Thr Ala Ser Tyr Phe Asp Tyr Trp Gly Gln Gly Val Met
        100                 105                 110

Val Thr Val Ser Ser
        115

<210> SEQ ID NO 100
<211> LENGTH: 112
<212> TYPE: PRT
<213> ORGANISM: Artificial Sequence
<220> FEATURE:
<222> LOCATION: (1)..(112)
<223> OTHER INFORMATION: Amino acid sequence of light chain variable
      region

<400> SEQUENCE: 100

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
            85                  90                  95

Thr His Val Leu Thr Phe Gly Ala Gly Thr Lys Leu Glu Leu Lys Arg
        100                 105                 110

<210> SEQ ID NO 101
<211> LENGTH: 120
<212> TYPE: PRT
<213> ORGANISM: Artificial Sequence
<220> FEATURE:
<222> LOCATION: (1)..(120)
<223> OTHER INFORMATION: Amino acid sequence of heavy chain variable
      region

<400> SEQUENCE: 101

Glu Val Leu Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
            50                  55                  60

Lys Gly Arg Phe Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                85                  90                  95

Ala Arg Gly Gly Phe Ile Thr Thr Val Gly Phe Ala Tyr Trp Gly Gln
                100                 105                 110

Gly Thr Leu Val Thr Val Ser Ala
                115                 120

<210> SEQ ID NO 102
<211> LENGTH: 113
<212> TYPE: PRT
<213> ORGANISM: Artificial Sequence
<220> FEATURE:
<222> LOCATION: (1)..(113)
<223> OTHER INFORMATION: Amino acid sequence of light chain variable
      region

<400> SEQUENCE: 102

Asp Val Val Thr Gln Thr Pro Leu Thr Leu Ser Val Thr Ile Gly
 1                   5                  10                  15

Gln Pro Ala Ser Ile Ser Cys Lys Ser Gln Ser Leu Leu Tyr Ser
                20                  25                  30

Asn Gly Lys Thr Tyr Leu Asn Trp Leu Leu Gln Arg Pro Gly Gln Ser
                35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Val Gln Gly
                85                  90                  95

Thr His Phe Pro Phe Thr Phe Gly Ser Gly Thr Lys Leu Glu Ile Lys
                100                 105                 110

Arg

<210> SEQ ID NO 103
<211> LENGTH: 118
<212> TYPE: PRT
<213> ORGANISM: Artificial Sequence
<220> FEATURE:
<222> LOCATION: (1)..(118)
<223> OTHER INFORMATION: Amino acid sequence of heavy chain variable
      region

<400> SEQUENCE: 103

Glu Val Gln Leu Gln Gln Ser Gly Pro Glu Leu Val Lys Pro Gly Ala
 1                   5                  10                  15

Ser Val Lys Ile Pro Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
                35                  40                  45

Gly Asp Ile Asn Pro Asn Asn Gly Gly Thr Ile Tyr Ser Gln Asn Phe
 50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Thr Ala Val Tyr Tyr Cys

```
                                    85                  90                  95
Ala Arg Phe Arg Val Tyr Tyr Ala Met Asp Tyr Trp Gly Gln Gly Thr
                    100                 105                 110

Ser Val Thr Val Ser Ser
            115

<210> SEQ ID NO 104
<211> LENGTH: 111
<212> TYPE: PRT
<213> ORGANISM: Artificial Sequence
<220> FEATURE:
<222> LOCATION: (1)..(111)
<223> OTHER INFORMATION: Amino acid sequence of light chain variable
      region

<400> SEQUENCE: 104

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Leu Thr Phe Gly Ala Gly Thr Lys Leu Glu Leu Lys
            100                 105                 110
```